(12) United States Patent
Haydock et al.

(10) Patent No.: US 7,074,558 B2
(45) Date of Patent: Jul. 11, 2006

(54) NUCLEIC ACID AMPLIFICATION USING AN RNA POLYMERASE AND DNA/RNA MIXED POLYMER INTERMEDIATE PRODUCTS

(75) Inventors: Paul V. Haydock, Shoreline, WA (US); Jack U'ren, Redmond, WA (US)

(73) Assignee: PBI Technology, Inc., Seattle, WA (US)

( * ) Notice: Subject to any disclaimer, the term of this patent is extended or adjusted under 35 U.S.C. 154(b) by 662 days.

(21) Appl. No.: 10/077,383

(22) Filed: Feb. 15, 2002

(65) Prior Publication Data

US 2003/0050444 A1 Mar. 13, 2003

Related U.S. Application Data

(60) Provisional application No. 60/296,812, filed on Jun. 7, 2001.

(51) Int. Cl.
*C12Q 1/68* (2006.01)
*C12P 19/34* (2006.01)

(52) U.S. Cl. ............... 435/6; 435/91.2; 435/91.21; 435/91.51

(58) Field of Classification Search ............... 435/6, 435/91.2, 91.21, 91.51
See application file for complete search history.

(56) References Cited

U.S. PATENT DOCUMENTS 5,766,849 A 6/1998 McDonough et al.

FOREIGN PATENT DOCUMENTS

WO WO 00/73486 A1 12/2000

OTHER PUBLICATIONS

Compton, J., "Nucleic acid sequence-based amplification," Nature, Mar. 1991, pp. 91-92, vol. 350.

*Primary Examiner*—Kenneth R. Horlick
*Assistant Examiner*—Joyce Tung
(74) *Attorney, Agent, or Firm*—Townsend and Townsend and Crew LLP

(57) ABSTRACT

This invention provides for a novel amplification procedure for nucleic acid. The method uses a wild type or mutant RNA polymerase designed to transcribe both deoxyribonucleotides and ribonucleotides.

30 Claims, 10 Drawing Sheets

*Amplification Cycle*

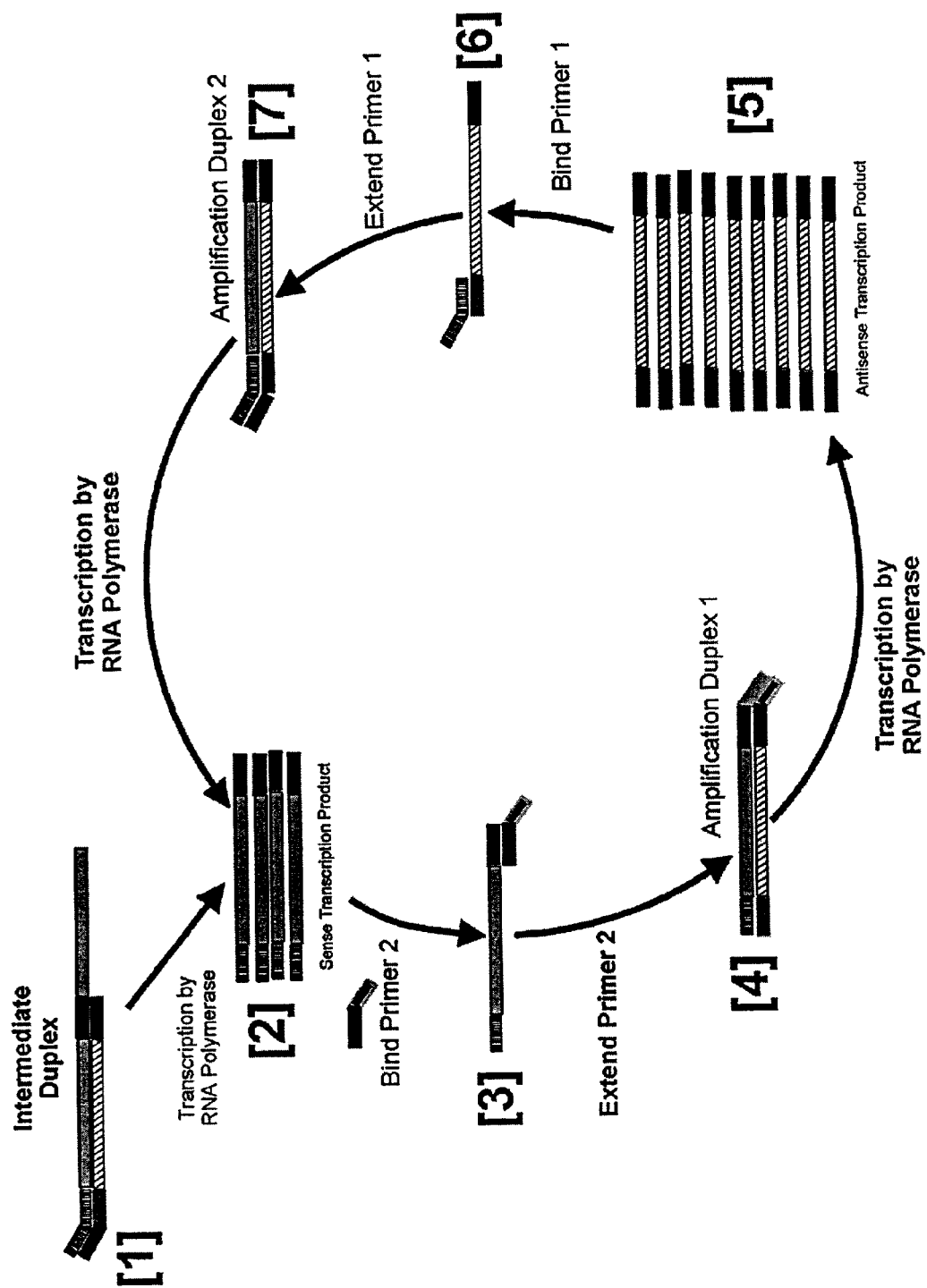
Figure 1 *Amplification Cycle*

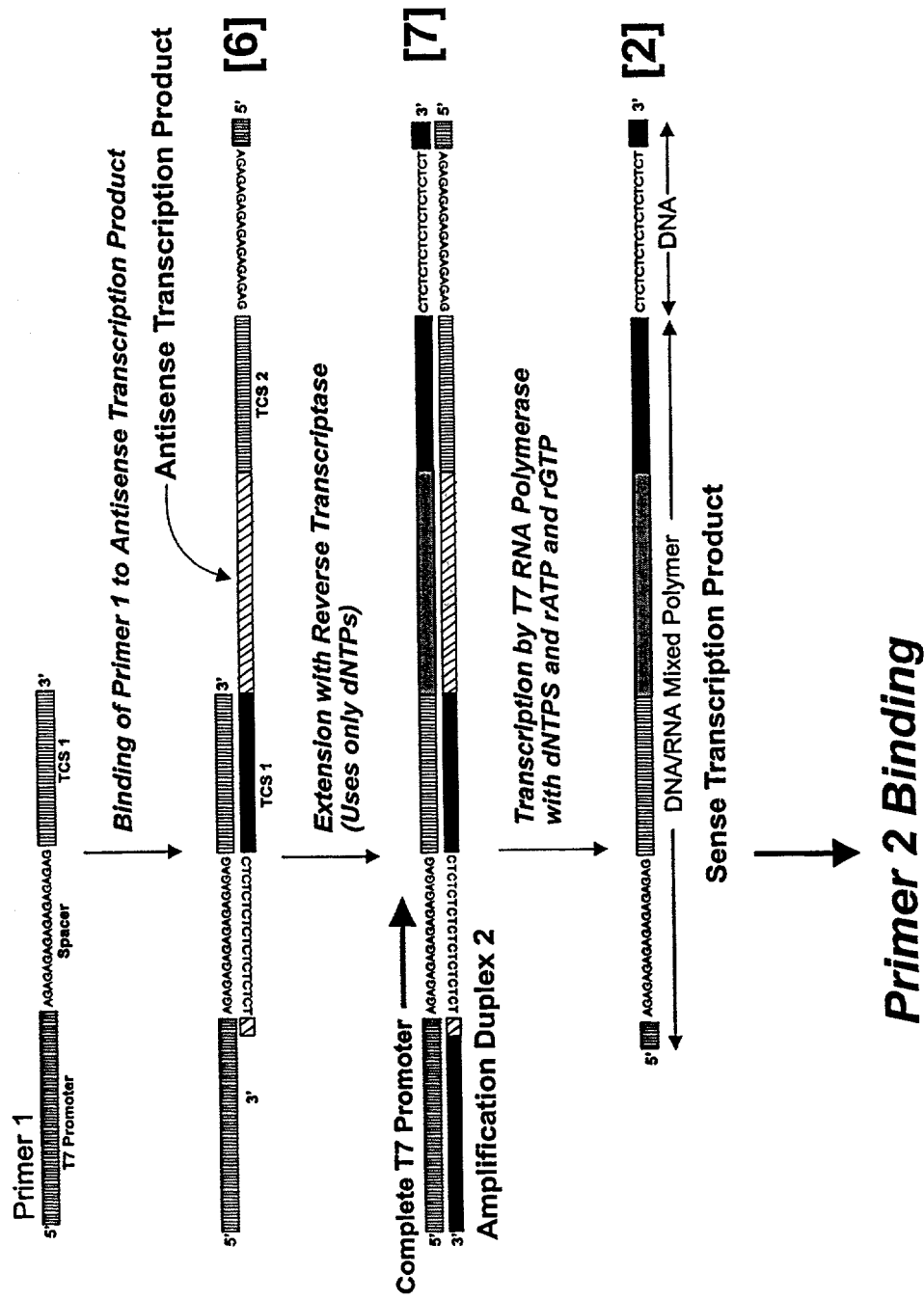
Figure 2 Detailed Description of the First Half of the Amplification Cycle

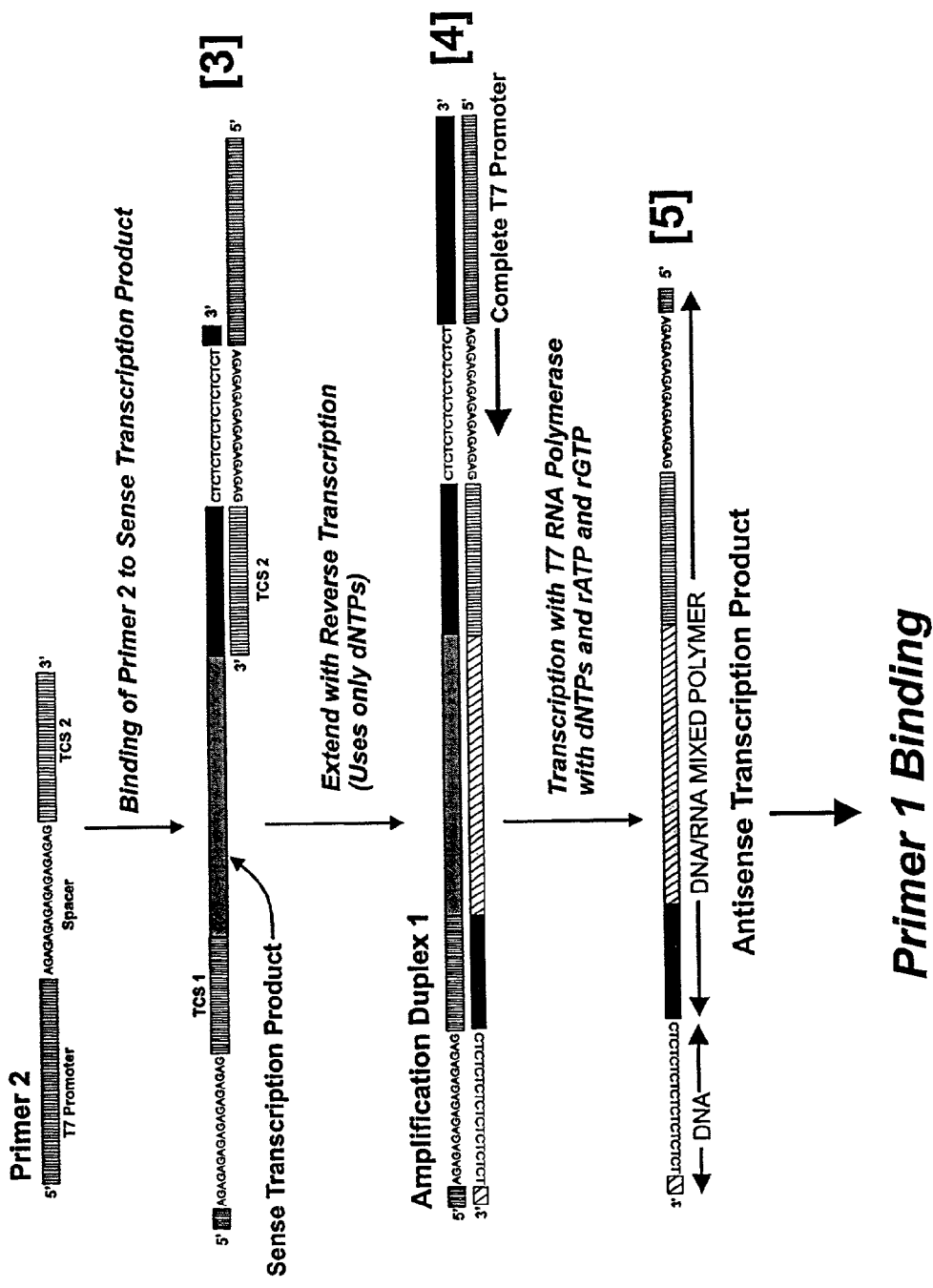
Figure 3  Detailed Description of the Second Half of the Amplification Cycle

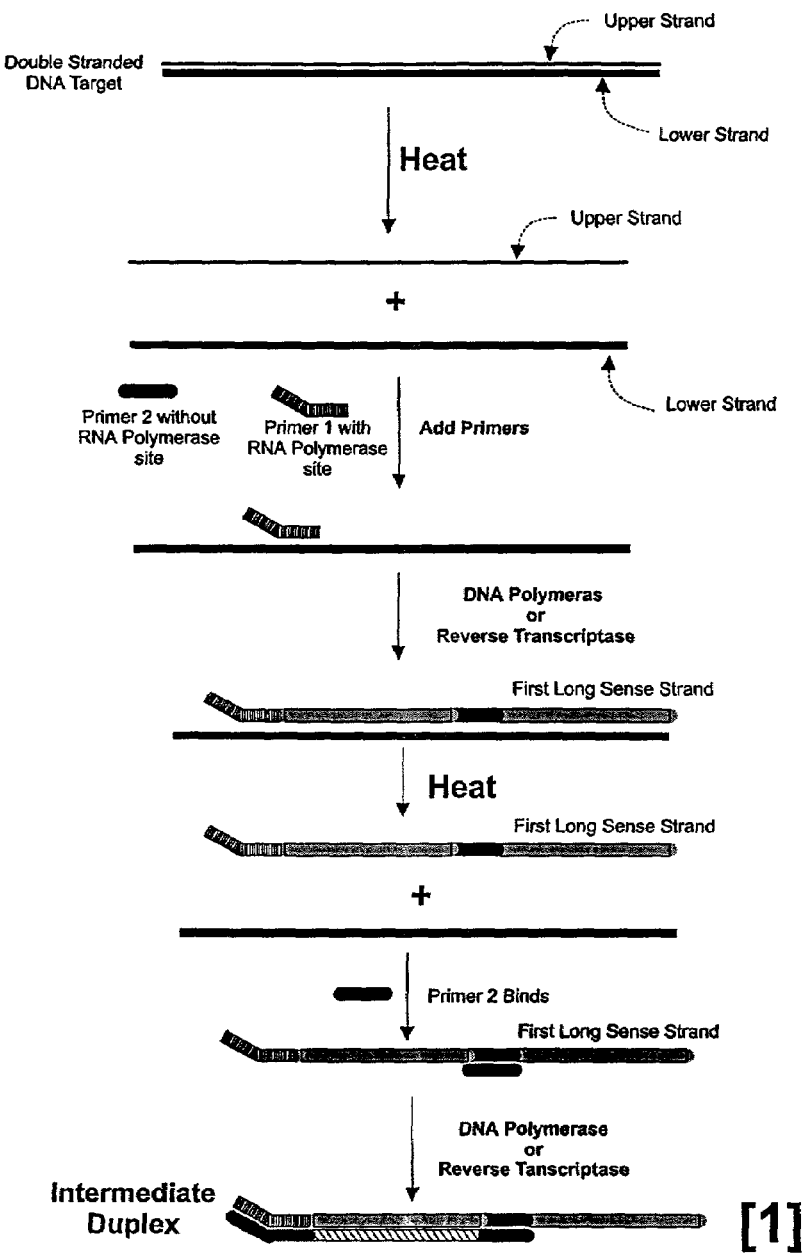
Figure 4 *Intermediate Duplex Formation from DNA with a Second Heating Step*

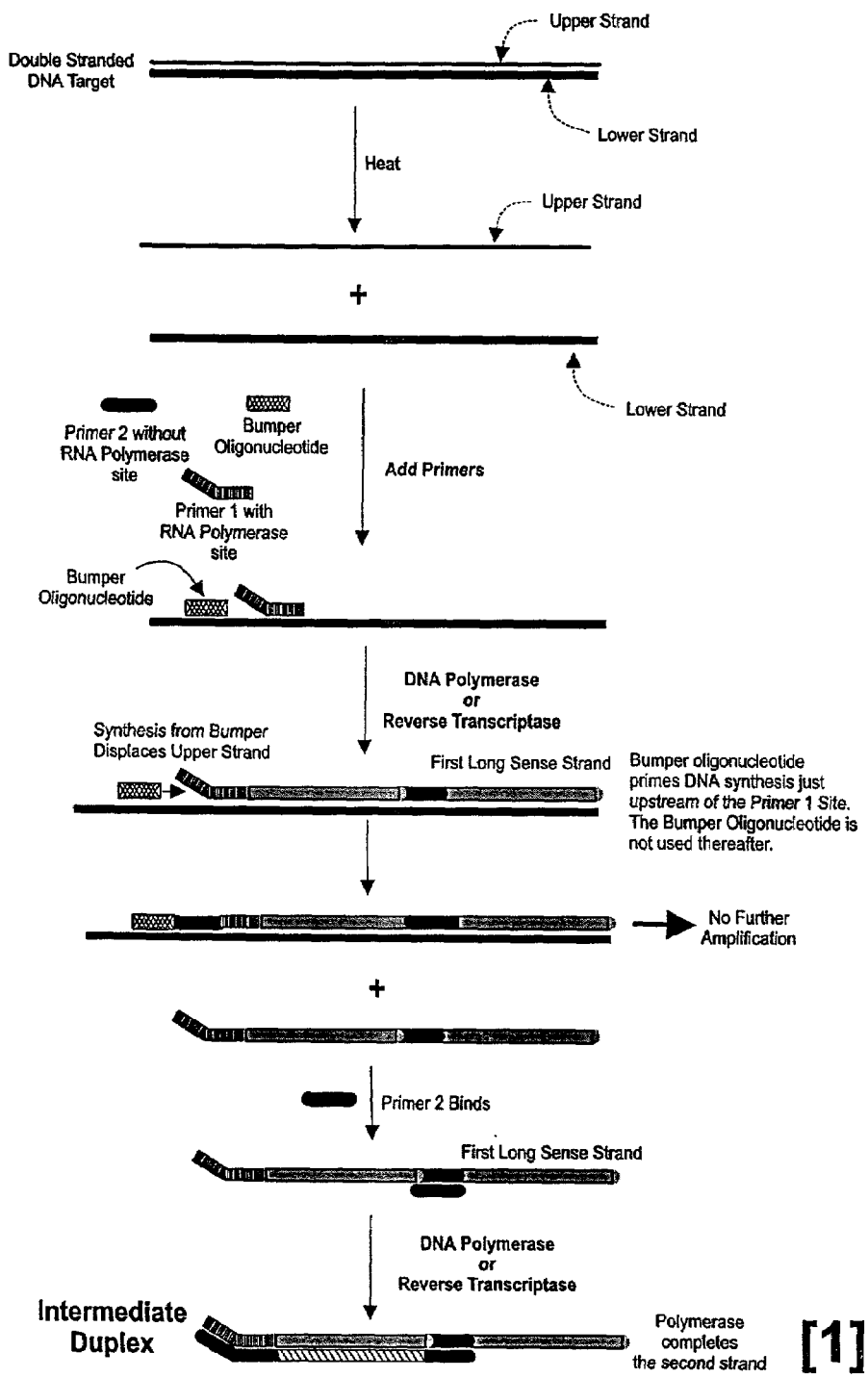
Figure 5 *Intermediate Duplex Formation Using a Bumper Oligonucleotide*

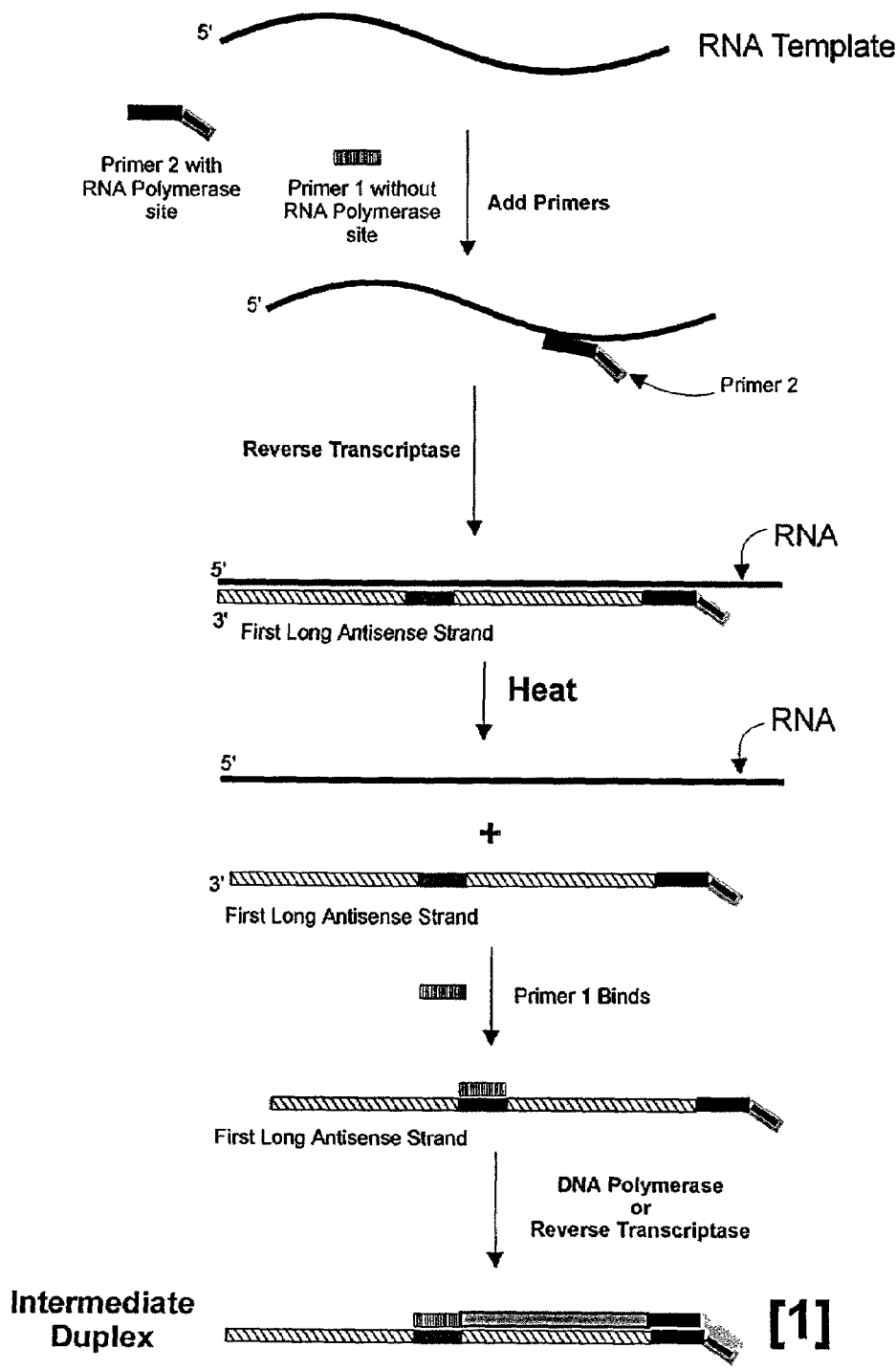
Figure 6 *Intermediate Duplex Formation from RNA Using a Heat Step*

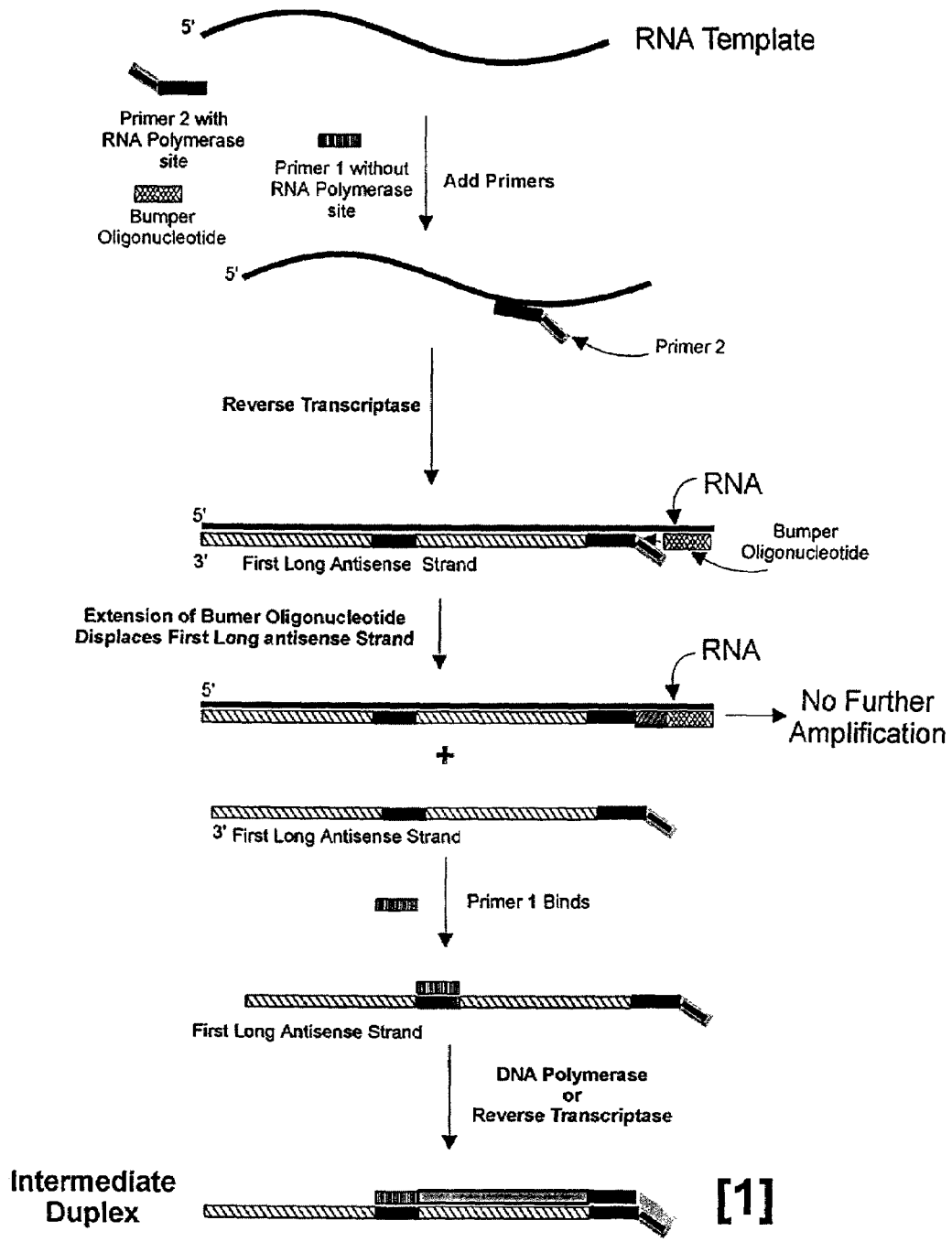
Figure 7 *Intermediate Duplex Formation from RNA Using a Bumper Oligonucleotide*

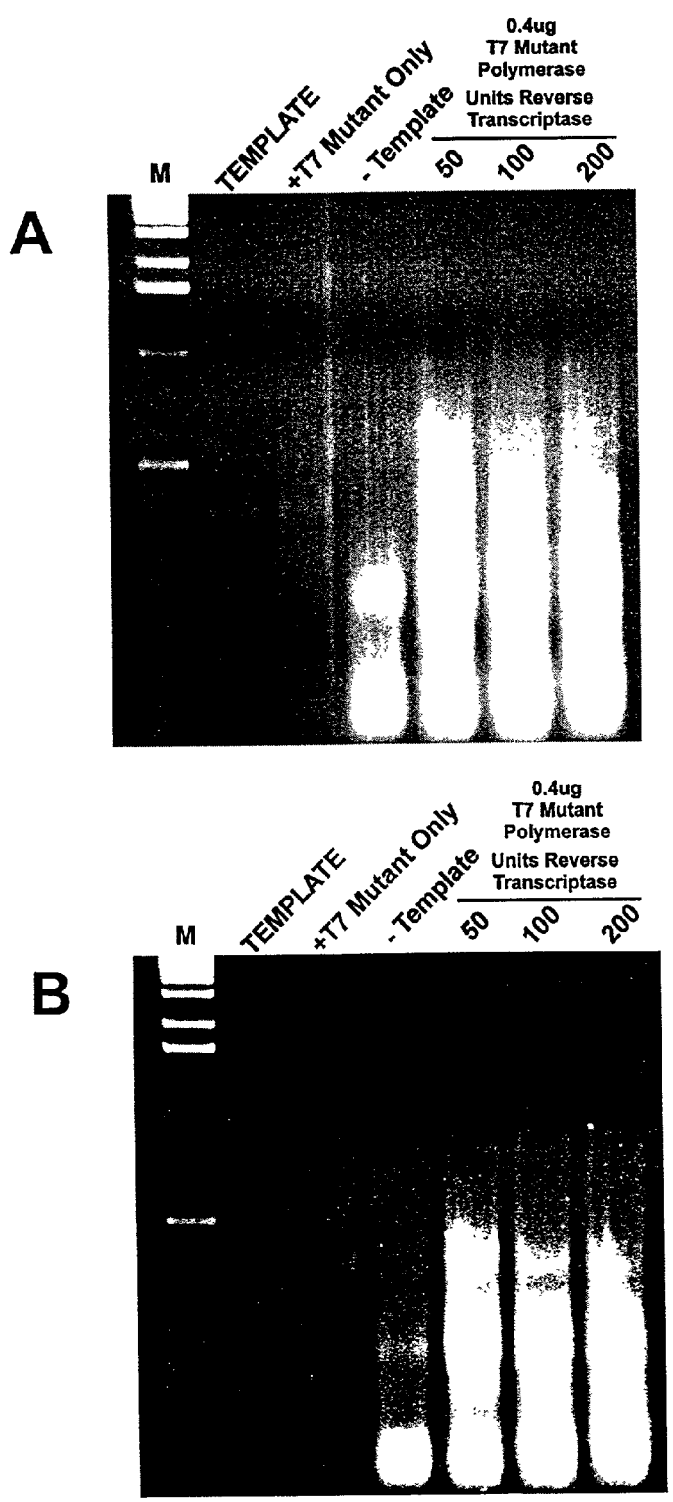
Figure 8 *Agarose Gel Electrophoretic Analysis of Amplification Products*

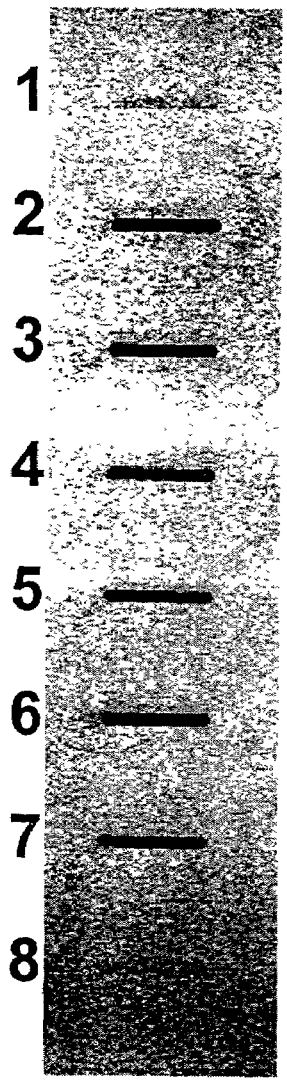
Figure 9 *Hybridization Analysis of Amplification Products*

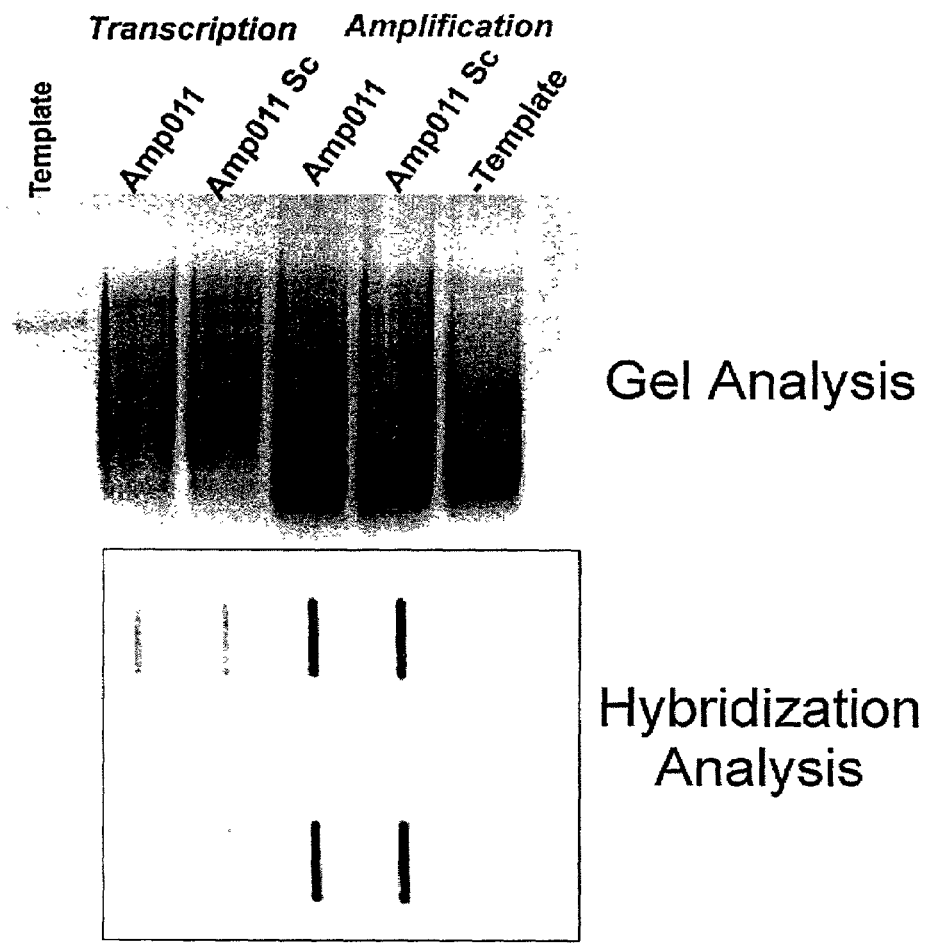
Figure 10 *Effect of Spacer Variation on Amplification Efficiency*

SEQUENCE LISTING

<160> NUMBER OF SEQ ID NOS: 33

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:T7
      phage-encoded RNA polymerase (RNAP) recognition
      sequence

<400> SEQUENCE: 1
taatacgact cactataggg aga                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:SP6
      phage-encoded RNA polymerase (RNAP) recognition
      sequence

<400> SEQUENCE: 2
atttaggtga cactatagaa gaa                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:T3
      phage-encoded RNA polymerase (RNAP) recognition
      sequence

<400> SEQUENCE: 3
aattaaccct cactaaaggg aga                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:K11
      phage-encoded RNA polymerase (RNAP) recognition
      sequence

<400> SEQUENCE: 4
aattagggca cactataggg aga                                              23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:(A)-12-20
      homopolymer spacer sequence
<220> FEATURE:
<221> NAME/KEY: modified_base
<222> LOCATION: (13)..(20)
<223> OTHER INFORMATION: a at positions 13-20 may be present or absent

<400> SEQUENCE: 5
aaaaaaaaaa aaaaaaaaaa                                                  20

<210> SEQ ID NO 6

```
<211> LENGTH: 20
<212> TYPE: DNA
<213> ORGANISM: Artificial Sequence
<220> FEATURE:
<223> OTHER INFORMATION: Description of Artificial Sequence:(T)-12-20
      homopolymer spacer sequence
<220> FEATURE:
<221> NAME/KEY: modified_base
<222> LOCATION: (13)..(20)
<223> OTHER INFORMATION: t at positions 13-20 may be present or absent

<400> SEQUENCE: 6
tttttttttt tttttttttt                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:(C)-12-20
      homopolymer spacer sequence
<220> FEATURE:
<221> NAME/KEY: modified_base
<222> LOCATION: (13)..(20)
<223> OTHER INFORMATION: c at positions 13-20 may be present or absent

<400> SEQUENCE: 7
cccccccccc cccccccccc                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:(G)-12-20
      homopolymer spacer sequence
<220> FEATURE:
<221> NAME/KEY: modified_base
<222> LOCATION: (13)..(20)
<223> OTHER INFORMATION: g at positions 13-20 may be present or absent

<400> SEQUENCE: 8
gggggggggg gggggggggg                                             20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:(XY)-n
      spacer sequence
<220> FEATURE:
<221> NAME/KEY: modified_base
<222> LOCATION: (13)..(20)
<223> OTHER INFORMATION: n at positions 13-20 may be present or absent
<220> FEATURE:
<221> NAME/KEY: modified_base
<222> LOCATION: (1)..(20)
<223> OTHER INFORMATION: n = a, g, c or t, where positions 1, 3, 5, 7,
      9, 11, 13, 15, 17 and 19 = X and positions 2, 4, 6, 8, 10,
      12, 14, 16, 18 and 20 = Y, in the formula (XY)-n, and
      where X and Y are independently selected from a, g, c
      or t, and X and Y are not the same

<400> SEQUENCE: 9
nnnnnnnnnn nnnnnnnnnn                                             20

<210> SEQ ID NO 10
<211> LENGTH: 16
<212> TYPE: DNA
<213> ORGANISM: Artificial Sequence
```

```
<220> FEATURE:
<223> OTHER INFORMATION: Description of Artificial Sequence:spacer
      sequence

<400> SEQUENCE: 10
aaagggaaga gagagg                                                    16

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence:spacer
      sequence

<400> SEQUENCE: 11
cttttttttc ttccc                                                     15

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence:spacer
      sequence

<400> SEQUENCE: 12 gcgcccgc                                                              8

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence:spacer
      sequence

<400> SEQUENCE: 13 atttaatt                                                              8

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence:spacer
      sequence

<400> SEQUENCE: 14 caaacccaa                                                             9

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:RNA
      polymerase (RNAP) active site consensus sequence
<220> FEATURE:
<221> NAME/KEY: MOD_RES
<222> LOCATION: (2)..(8)
<223> OTHER INFORMATION: Xaa = any amino acid

<400> SEQUENCE: 15

Lys Xaa Xaa Xaa Xaa Xaa Xaa Xaa Tyr Gly Ser
 1               5                  10
```

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence:AMP010
    Amplification Primer

<400> SEQUENCE: 16
aatttaatac gactcactat agggagagag agagagagac tcctaaagtc actcctaacg    60

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence:AMP011
    Amplification Primer

<400> SEQUENCE: 17
aatttaatac gactcactat agggagagag agagagagag ctattcgccg tgtccctctc    60
g                                                                    61

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence:AMP011S
    Amplification Primer

<400> SEQUENCE: 18
aatttaatac gactcactat agggagaagg agaaaaagag ctattcgccg tgtccctctc    60
g                                                                    61

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:AMP012 PCR
    Primer

<400> SEQUENCE: 19
gctattcgcc gtgtccctct cg                                              22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:AMP013 PCR
    Primer

<400> SEQUENCE: 20
ctcctaaagt cactcctaac g                                               21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Bump003
    Bumper Primer

<400> SEQUENCE: 21

```
ctgtgtccct atctgttaca                                                    20
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:AMPSig5-B
      Signal Oligonucleotide

<400> SEQUENCE: 22

```
ccatcctaaa gccaacacct aa                                                 22
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:AMPSig5AS-B
      Signal Oligonucleotide

<400> SEQUENCE: 23

```
ttaggtgttg gctttaggat gg                                                 22
```

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence:T7 Promoter

<400> SEQUENCE: 24

```
aatttaatac gactcactat agggagagag agagagaga                               39
```

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence:T7 Promoter
      S

<400> SEQUENCE: 25

```
aatttaatac gactcactat agggagaagg agaaaaaga                               39
```

<210> SEQ ID NO 26
<211> LENGTH: 375
<212> TYPE: DNA
<213> ORGANISM: Artificial Sequence
<220> FEATURE:
<223> OTHER INFORMATION: Description of Artificial Sequence:Amplicon
      model template

<400> SEQUENCE: 26

```
aatttaatac gactcactat agggagagag agagagagac tcctaaagtc acctcctaac        60
gtccatccta agccaacac ctaaagccta cacctaaaga cccatcaagt caacgcctat        120
cttaaagttt aaacataaag accagaccta agaccagact ctaaagacac tacataaaga       180
ccagacctaa agacgccttg ttgttagcca taagtgata acctttaatc attgtcttta        240
ttaatacaac tcactataag gagagacaac ttaaagagac ttaaagatt aatttaaaat        300 ttatcaaaaa gagtattgac ttaaagtcta acctatagga tacttacagc catcgagagg       360
gacacggcga atagc                                                        375
```

```
<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:spacer
      sequence standard structure of AMP011 Primer

<400> SEQUENCE: 27
gggagagaga gagagaga                                                    18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:spacer
      sequence variant modified structure of AMP011Sc Primer

<400> SEQUENCE: 28
gggagaagga gaaaaaga                                                    18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:(XY)-n
      spacer sequence, where X = a and Y = g
<220> FEATURE:
<221> NAME/KEY: modified_base
<222> LOCATION: (13)..(20)
<223> OTHER INFORMATION: a or g at positions 13-20 may be present or
      absent

<400> SEQUENCE: 29
agagagagag agagagagag                                                  20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:(X)-n spacer
      sequence
<220> FEATURE:
<221> NAME/KEY: modified_base
<222> LOCATION: (1)..(20)
<223> OTHER INFORMATION: n = a, g, c or t, where positions 1-20 are all
      the same nucleotide
<220> FEATURE:
<221> NAME/KEY: modified_base
<222> LOCATION: (13)..(20)
<223> OTHER INFORMATION: n at positions 13-20 may be present or absent

<400> SEQUENCE: 30
nnnnnnnnnn nnnnnnnnnn                                                  20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:(XY)-n
      spacer sequence, where X = a, Y = g and n = 9

<400> SEQUENCE: 31
agagagagag agagagag                                                    18
```

```
<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:(XY)-n
      spacer sequence complement, where X = a, Y = g and n = 9

<400> SEQUENCE: 32
ctctctctct ctctctct                                                    18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:(X)-n spacer
      sequence, where n = 18
<220> FEATURE:
<221> NAME/KEY: modified_base
<222> LOCATION: (1)..(18)
<223> OTHER INFORMATION: n = a, g, c or t, where positions 1-18 are all
      the same nucleotide

<400> SEQUENCE: 33
nnnnnnnnnn nnnnnnnn                                                    18
```

NUCLEIC ACID AMPLIFICATION USING AN RNA POLYMERASE AND DNA/RNA MIXED POLYMER INTERMEDIATE PRODUCTS

CROSS REFERENCES TO RELATED APPLICATIONS

Not Applicable.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

Many forms of nucleic acid amplification reactions have been developed in recent years. The first method was the Polymerase Chain Reaction (PCR) which involved repeated cycles/ of heating to separate the DNA strands, primer annealing to the strands, and primer extension by a DNA polymerase. Product accumulation from the PCR reaction is exponential; that is, the amount of product doubles for every cycle of amplification. Therefore, the expected amount of product may be calculated by the formula (Eff*2)n where Eff is the efficiency of the primer annealing and primer extension reaction, and n is the number of cycles.

An alternative method for target amplification was developed called NASBA (Nucleic Acid Sequence Based Amplification) (see e.g., Compton (1991) *Nature* 350: 91–92). This method relies on the concerted action of three enzymatic activities, Reverse transcriptase, RNaseH, and RNA Polymerase, to amplify an RNA target. Reverse transcriptases generally possess an endogenous RNase H activity, which can under the correct conditions, substitute for exogenously added RNase H activity. Primers are first designed which have an RNA polymerase site together with a target recognition sequence. Then, the primers are added to the target nucleic acid together with the three enzyme activities. First, primer binds followed by primer extension across the sequence of interest. The result is a double-stranded RNA-DNA hybrid. The RNA portion of the hybrid is digested by the RNase H activity allowing binding of the other primer. The reverse transcriptase activity then extends this primer back across the sequence of interest finishing at the RNA polymerase binding sequence. The RNA polymerase activity then transcribes the sequence of interest making multiple single-stranded RNA copies. These RNAs may bind more primers and the cycle continues. Because each transcription step yields 10–100 copies of RNA per copy of template, product accumulates rapidly and logarithmically.

Still, another method has been developed which is called SDA or strand Displacement Amplification (see e.g., Walker (1993) *PCR Meth. Appl.* 3: 1–6. This method utilizes four primer sequences with two primers binding on either end of the sequence of interest. It also requires a DNA polymerase and a restriction endonuclease (A restriction endonuclease binds to a specific sequence called its recognition site, and then cleaves the DNA a specific sequence). In the first step, nucleic acid strands are heat separated allowing the binding of the first primer pair. The inner primer contains a restriction enzyme site which is non-complementary to the target sequence, while the outer primer binds just upstream of the inner primer. DNA polymerase extends both primers, but extension from the outer primer displaces the newly synthesized inner strand yielding a single strand template for primer binding. Extension reactions are done in the presence of a nucleotide analog (alpha-thio-dATP such that the newly synthesized strands are fully substituted making them immune to cleavage by the restriction endonuclease. However, since the inner primers are not substituted, and the complement of the inner primer is substituted, the restriction enzyme will create a nick within the inner primer sequence by cutting only within the unsubstituted sequence. The nick can act as a priming site for DNA polymerase. In the process of extending the nick, the DNA strands are separated or displaced by the DNA polymerase creating single strand primers which can then bind inner primers for the next round of amplification. Accumulation of product for SDA is therefore exponential since every priming event doubles the amount of product.

Other amplification schemes have been devised, but they all require generating a single strand intermediate that allows primer binding for continued rounds of amplification (see e.g., Fahy et al. (1991) *PCR Meth. Appl.* 1: 25–33; Guatelli et al. (1990) *Proc. Nat. Acad. Sci., U.S.A.* 87: 1874–1878. While the methods described above have been shown to work well, they do have some drawbacks. PCR requires the use of a thermocycler to obtain rounds of strand separation and primer extension. Furthermore, the process of heating and cooling can be slow resulting in a PCR reaction requiring a few hours to complete from start to finish. NASBA circumvents this issue by being run isothermally, that is at a single temperature. The products are single-stranded RNA which can be relatively unstable especially if an RNase activity, which are ubiquitous, is inadvertently introduced. RNA products are also generally chemically less stable. Furthermore, the length of the expected product dictates the efficiency of the amplification reaction. This is in part due to the RNAaseH activity which can inactivate RNA transcripts with bound primers. NASBA reactions also require the addition of high concentrations of both ribonucleotides and deoxyribonucleotides increasing the cost of running a reaction. NASBA reactions are also run at lower temperatures leading to the production of spurious amplification products. In SDA, while the amplification products are DNA, the products are modified by the presence of the alpha-thio-dATP used to inhibit strand cleavage by the restriction endonuclease which may make further manipulation of the product difficult, especially in research applications.

There is a need for improved methods of nucleic amplification. This invention meets those needs.

SUMMARY OF THE INVENTION

In one aspect, the present invention provides for oligonucleotide primers that comprise in the following order from 5' to 3': a phage-encoded RNA polymerase recognition sequence, a spacer sequence comprising a sequence of from 12 to 20 nucleotides that consists of one nucleotide type or two different nucleotide types, and a target complementary sequence which can bind a segment of a target nucleic acid. In certain embodiments, the spacer sequence comprises a nucleotide sequence having the formula $(XY)_n$, wherein n is from 6 to 10, wherein X and Y are independently selected from the group consisting of an adenine nucleotide, a guanine nucleotide, a cytosine nucleotide, and a thymidine nucleotide, wherein X and Y are not the same (SEQ ID NO:9). In certain preferred embodiments, X is an adenine nucleotide and Y is a guanine nucleotide (SEQ ID NO:29). In other embodiments, the spacer sequence comprises a nucleotide sequence having the formula $(X)_n$, wherein n is from 12 to 20, wherein X is selected from the group consisting of an adenine nucleotide, a guanine nucleotide, a cytosine nucleotide, and a thymidine nucleotide (SEQ ID NO:30).

In another aspect, the present invention provides for methods of amplifying a target nucleic acid in an aqueous solution with a first and a second primer, said method comprising:

i.) transcribing an intermediate duplex with a phage-encoded RNA polymerase to form a sense transcription product having a 5' end and a 3' end, wherein said intermediate duplex comprises a double-stranded molecule, wherein said double-stranded DNA molecule comprises a first and a second strand, wherein said first strand comprises in the following order from 5' to 3: a phage-encoded RNA polymerase recognition sequence, a first spacer sequence comprising a sequence of from 12 to 20 nucleotides that consists of one nucleotide type or two different nucleotide types, and a first target complementary sequence which can bind to a segment of said target nucleic acid, wherein said second strand comprises in the following order from 5' to 3': a second target complementary sequence which can bind to a segment of said target nucleic acid, a second spacer sequence comprising a sequence of from 12 to 20 nucleotides that consists of one nucleotide type or two different nucleotide types, and a phage-encoded RNA polymerase recognition sequence, wherein said transcribing takes place in the presence of $Mn^{++}$, with all four dNTPs, and with those rNTPs represented in said first spacer sequence;

ii.) hybridizing said second primer to said sense transcription product to form a second primer-sense transcription product complex, wherein said second primer comprises in the following order from 5' to 3': a phage-encoded RNA polymerase recognition sequence, said second spacer sequence, and said second target complementary sequence which can bind to a 3' segment of said target nucleic acid;

iii.) extending said second primer-sense transcription product complex with a Reverse Transcriptase that lacks RNAseH activity to form a first amplification duplex;

iv.) transcribing said first amplification duplex with a phage-encoded RNA polymerase, in the presence of $Mn^{++}$, with all four dNTPs, and with those rNTPs represented in said second spacer sequence, to form an antisense transcription product;

v.) hybridizing said first primer to said antisense transcription product to form a first primer-antisense transcription product complex,wherein said first primer comprises in the following order from 5' to 3': a phage-encoded RNA polymerase recognition sequence, said first spacer sequence, and said first target complementary sequence which can bind to a 5' segment of said target nucleic acid;

vi.) extending said second primer-antisense transcription product complex with a Reverse Transcriptase that lacks RNAseH activity to form a second amplification duplex; and vii.) transcribing said second amplification duplex with a phage-encoded RNA polymerase, in the presence of $Mn^{++}$, with all four dNTPs, and with those rNTPs represented in said first spacer sequence to form said sense transcription product.

Typically, these methods further involve repetitively carrying out steps i to vii. For example, steps i to vii can be carried out one, two, etc. When the tirst or second spacer comprises a nucleotide sequence having the formula $(XY)_n$ (SEQ ID NO:9), as described above, then the rNTPs represented in the spacer sequences should be present in the reaction mixture. For example if a spacer sequence is $(AG)_{12-20}$ (SEQ ID NO:5) then rATP and rGTP should be present in the reaction mixture. Similarly, the first or said second spacer sequence can comprise a nucleotide sequence having the formula $(X)_{12-20}$ (SEQ ID NO:30), where X is a dNTP. Then, the corresponding rNTP should be present in the reaction mixture.

The sense and antisense transcription products can comprise a nucleic acid strand comprising both ribonucleotides and deoxyribonucleotides. In addition, the first and said second amplification duplexes can consist of deoxyribonucleotides and ribonucleotides.

In certain embodiments, the intermediate duplex comprises a double-stranded DNA comprising one complete primer sequence followed by the entire sequence that is to amplified. The intermediate duplex can be formed from a variety of sources including, without limitation, double-stranded DNA, single-stranded DNA, or RNA. For example, in certain embodiments, the intermediate duplex is formed by the process comprising the following steps of: denaturing a double-stranded DNA target to form an upper strand and a lower strand; hybridizing the first primer to the lower strand to form a first primer-lower strand complex; extending the first primer-lower strand complex with a Reverse Transcriptase that lacks RNAseH activity or with a DNA Polymerase to form a first long sense strand product-lower strand complex; denaturing the first long sense strand product-lower strand complex into a first long sense strand product and the lower strand; hybridizing the second primer to the first long sense strand product to form a second primer-first long sense strand product; and extending the first primer-first long antisense strand product with a Reverse Transcriptase that lacks RNAseH activity or with a DNA Polymerase to yield the intermediate duplex (see e.g., FIG. 4).

In other embodiments, the intermediate duplex is formed from DNA by the process comprising the following steps of: denaturing a double-stranded DNA target to form an upper strand and a lower strand; hybridizing the first primer to the lower strand to form a first primer-lower strand complex; extending the first primer-lower strand complex with a Reverse Transcriptase that lacks RNAseH activity or with a DNA Polymerase to form a first long sense strand product-lower strand complex, wherein the first long sense strand product has a 5' and a 3' end; displacing the first sense strand product from the lower strand by: hybridizing a bumper oligonucleotide to a subsequence on the lower strand adjacent to the 5' end of the first sense strand product on the first sense strand product-lower strand complex; extending the bumper oligonucleotide with a Reverse Transcriptase that lacks RNAseH activity or with a DNA Polymerase, thereby displacing the first sense strand product; hybridizing the second primer to the first long sense strand product to form a second primer-first long sense strand product; and extending the first primer-first long antisense strand product with a Reverse Transcriptase that lacks RNAseH activity or with a DNA Polymerase to yield the intermediate duplex (see e.g., FIG. 5).

In still other embodiments, the intermediate duplex is formed from RNA. For example, the intermediate duplex can be formed by the process comprising the following steps of: hybridizing the second primer to a target RNA molecule to form a second primer-RNA template complex; extending the second primer-target RNA molecule complex with a Reverse Transcriptase that lacks RNAseH activity or a DNA Polymerase to form a first long antisense strand product-template complex, wherein the first long antisense strand product has a 5' and a 3' end; displacing the first long antisense strand product from the target RNA molecule by:

hybridizing a bumper oligonucleotide to a subsequence on the target RNA molecule adjacent to the 5' end of the first sense strand product on the first sense strand product-lower strand complex; extending the bumper oligonucleotide with a Reverse Transcriptase that lacks RNAseH activity or with a DNA Polymerase, thereby displacing the first long antisense strand product; hybridizing the first primer to the first long antisense strand product to form a first primer-first long antisense strand product complex; and extending the first primer-first long antisense strand product with a Reverse Transcriptase that lacks RNAseH activity or with a DNA Polymerase to yield the intermediate duplex (see e.g., FIG. 6).

In still other embodiments, the intermediate duplex can be formed by the process comprising the following steps of: hybridizing the second primer to a single-stranded target RNA molecule to form a second primer-RNA template complex; extending the second primer-RNA template complex with a Reverse Transcriptase that lacks RNAseH activity or a DNA Polymerase to form a first long antisense strand product-template complex; denaturing the first long antisense strand product-RNA template complex into a first long antisense strand product and the single-stranded RNA molecule; hybridizing the first primer to the first long antisense strand product to form a first primer-first long antisense strand product complex; and extending the first primer-first long antisense strand product with a Reverse Transcriptase that lacks RNAseH activity or with a DNA Polymerase to yield the intermediate duplex (see e.g., FIG. 7).

The temperature of the reaction mixture can vary over the range at which the enzymes in the mixture are active and products are produced. However, the methods can be carried out at a single temperature, e.g., isothermally. For example, the methods can be carried out at a single temperature of between 25° C. and 55° C., or at a single temperature of greater than 50° C.

The methods described herein can comprise a reaction mixture further containing a bumper oligonucleotide which is: (i) able to hybridize to a DNA sequence about or adjacent to the 5' end of the first long strand and (ii) able to serve as polymerase primer which displaces the first long strand when extended towards the 3' end of the target nucleic acid.

This invention further comprises a novel composition comprising a double-stranded DNA having a first and second end comprising a phage-encoded RNA polymerase recognition sequences on both the first and second ends wherein at least one end has a complementary sequence that forms a phage polymerase recognition site. This is termed an intermediate duplex. The composition may also be a double-stranded DNA having phage-encoded RNA polymerase recognition sequences on both the first and second ends wherein the sites may be the same or different. The composition may also have a single functional RNA polymerase binding site on one end and a blunt end on the other end in which the blunt end has the target complementary sequence with the RNA polymerase binding site. The composition may optionally comprise a signature sequence for a specific genus or species of organism.

This invention also provides for a novel aqueous reaction mixture comprising: i. a target nucleic acid for amplification; ii. a first and second amplification primer each having a phage-encoded RNA polymerase recognition sequence, a spacer unit of 12 to 20 bases or more, and a target binding sequence wherein the first target binding sequence is complementary to the 5' end of the target sequence and the second target binding sequence is complementary to the antisense sequence of the 3' end of the target sequence; iii. phage-encoded RNA polymerase either wild type or an RNA polymerase mutated to recognize and polymerize dNTP and rNTP; and, iv. an excess of dNTPs and 1 or 2 rNTPs. The reaction mixture may also comprise target nucleic acid which is a double-stranded DNA having a first 5' end which bears a phage-encoded RNA polymerase recognition site and a second 5' end which bears a phage-encoded RNA polymerase recognition sequence.

Essentially any RNA polymerase that is active under the method conditions and can transcribe rNTPs and dNTPs into the products in the method can be used. An especially preferred class of RNAPs are the phage-encoded polymerases which include, without limitation, a T7 RNA polymerase, a T4 RNA polymerase, a T3 RNA polymerase, a SP6 RNA polymerase and a K11 RNA polymerase. In certain embodiments, the phage-encoded RNA polymerase is a mutant phage-encoded RNA polymerase (e.g., a mutated T7 RNAP) that is competent to incorporate dNTPs into a template nucleic acid. For example, T7 RNAPs with a Y639F mutation, or a S641A mutation, or Y639F/S641A mutations can be used. In certain embodiments, the T7 RNAP contains at least two mutations.

Manganese ions are critical in the method for the incorporation of dNTPs into the transcription products. Preferably, the $Mn^{++}$ is present in a concentration of between 10 μM to 20 mM. In an especially preferred embodiment, the concentration is 10 mM.

The target nucleic acid can be single-stranded DNA or comprised of RNA.

In some embodiments, one or more of the products of the method can be detected using a labeled reagent. For example, the methods can further comprise the sense transcription product, the antisense transcription product, the first amplification duplex, or the second amplification duplex, wherein the detecting comprises hybridizing a detection oligonucleotide comprising a detectable moiety, wherein the detection oligonucleotide is complementary to a subsequence of the sense transcription product, the antisense transcription product, the first amplification duplex, or the second amplification duplex.

This invention further provides for a kit for amplifying a target nucleic acid comprising a container containing a first primer having a sequence complementary to a 5' end of the target nucleic acid and a phage polymerase recognition sequence and a spacer sequence of 12 to 20 bases or more, and a container containing a second primer having a sequence which is the anti-complement to the 3' end of the target nucleic acid and a phage polymerase recognition sequence and a second spacer of 12 to 20 bases or more. The kit may also have a wild type RNA polymerase or a mutant phage polymerase competent to incorporate dNTP and rNTP simultaneously into a template nucleic acid. The kit may also have a bumper oligonucleotide which is able to hybridize to a template DNA sequence where that sequence is about or immediately adjacent to the 3' base of the sequence to which one of the amplification primers binds.

BRIEF DESCRIPTION OF THE DRAWINGS

FIG. 1 is a schematic of an embodiment of an amplification method described in this application. The cycle starts at the point of formation of the intermediate duplex [1].

FIG. 2 depicts an embodiment of the first half of the amplification cycle from primer binding to the antisense transcription product through production of sense transcription product. The entry point into the amplification cycle from the intermediate duplex is through the sense transcription product. Spacer sequences=SEQ ID NOS:31 and 32.

FIG. 3 depicts an embodiment of the second half of the amplification cycle from primer binding to the sense transcription product through production of antisense transcription product. The amplification cycle consists of alternating between production of sense transcription products and antisense transcription products. Spacer sequences=SEQ ID NOS:31 and 32.

FIG. 4 is a schematic of an embodiment for the formation of the intermediate duplex starting with a double-stranded DNA target. This embodiment utilizes two heating steps to denature the double strand DNA target, and dissociating the first long sense strand from the template.

FIG. 5 is a schematic of an embodiment for the formation of the intermediate duplex starting with a double-stranded DNA target that utilizes the bumper oligonucleotide to dissociate the first long sense strand from the template strand.

FIG. 6 is a schematic of an embodiment for the formation of the intermediate duplex starting with an RNA template and utilizing a heating step to dissociate the first long antisense strand (+) from the template RNA after the reverse transcription step.

FIG. 7 is a schematic of an embodiment for the formation of the intermediate duplex starting with an RNA strand, utilizing the bumper oligonucleotide to dissociate the first long antisense strand from the RNA strand after the reverse transcription step.

FIG. 8 shows the results of a typical amplification reaction.

FIG. 9 shows the results of an amplification analyzed by calorimetric slot blot hybridization.

FIG. 10 shows the results of a complete experiment comparing two amplification primers containing different spacer regions.

DEFINITIONS

A "spacer sequence" is a nucleotide sequence comprising any arrangement of one or two different nucleotides.

A "target complementary sequence" is a nucleotide sequence which can bind to a segment of a target nucleic acid. One of skill in the art can readily determine a "target complementary sequence" that can bind to a target nucleic acid under the reaction conditions being used.

The term "amplifying" refers to a process whereby a portion of a nucleic acid is replicated. Unless specifically stated "amplifying" or "copying" may refer to a single replication or arithmetic, logarithmic, or exponential amplification.

The term "detecting" refers to quantitatively or qualitatively determining the presence or absence of an analyte, such as a nucleic acid.

A "detection oligonucleotide" is an oligonucleotide that comprises a detectable moiety.

The term "detectable moiety" refers to a moiety that is attached through covalent or non-covalent means to the non-target antisense primer or said non-target sense-primer. A "detectable moiety" can be a radioactive moiety, a fluorescent moiety, a chemiluminescent moiety, an antibody moiety, etc.

The term "fluorescent moiety" refers to label that accepts radiant energy of one wavelength and emits radiant energy of a second wavelength.

A "positive control target nucleic acid" is a target nucleic acid that is known to be amplified under a particular set of reaction conditions.

"Amplification duplex" refers to a double-stranded DNA having a phage-encoded RNA polymerase recognition site at one end and primer complementary sequences at both ends. The amplification duplex is transcribed by the polymerase to produce multiple copies of its sense strand or antisense strand, depending on which end of the amplification duplex that the phage polymerase site is located.

"Amplification primer" refers to a nucleic acid sequence which has a subsequence, referred to as the TCS or Target Complementary sequence, which complements either the 5' end or the 3' antisense end of a target nucleic acid and further comprises a phage-encoded RNA polymerase recognition sequence. A spacer element of 12 to 20 bases or more is included between the phage promoter and the TCS.

"Double-stranded DNA" refers to a duplex of two complementary DNA strands which by convention is drawn as a double line with a sense strand from 5' to 3' as the top strand and an antisense strand from 3' to 5' as the bottom strand.

"Isothermal amplification method" refers to a process of repetitively copying a target nucleic acid without using heat to separate the strands of any duplex formed during the process. This would not include the original target nucleic acid which if double-stranded must be heat separated before the amplification process begins.

The phrase "nucleotide type" refers to a deoxyribonucleotide, e.g., dA, dT, dC, and dG. Thus, "one nucleotide type" would be dA, dT, dC, or dG. Examples of spacer sequences of one nucleotide type include, without limitation, $(A)_{12-20}$ (SEQ ID NO: 5), $(T)_{12-20}$ (SEQ ID NO: 6), $(C)_{12-20}$ (SEQ ID NO: 7), and $(G)_{12-20}$ (SEQ ID NO: 8). Examples of "two different nucleotide types" include dA and dT; dA and dC; dA and dG; dT and dC; dT and dG; or dC and dG. Thus, a spacer that consists of "two different nucleotide types" can be of the formula $(XY)_n$. (SEQ ID NO: 9). Alternatively, a spacer that consists of "two different nucleotide types" includes, without limitation, the following sequences: AAAGGGAAGAGAGAGG (SEQ ID NO: 10), CTTTTTTTTCTTCCC (SEQ ID NO: 11), GCGCCCGC (SEQ ID NO: 12), ATTTAATT (SEQ ID NO: 13), CAAAC-CCAA (SEQ ID NO: 14), etc.

"Phage-encoded RNA polymerase recognition site" refers to a double-stranded nucleic acid sequence to which a phage-encoded RNA polymerase will bind and transcribe a copy of the antisense strand. The recognition site is not copied during this transcription process and results in a primeness copy of the original antisense strand.

"Phage-encoded RNA polymerase recognition sequence" refers to a sense nucleic acid sequence which is read from 5' to 3' and which is recognized by a polymerase as a binding site and initiation point for transcription when duplexed with the corresponding antisense recognition sequence. Phage-encoded RNA polymerases each have their own specific recognition sequences. The term "phage-encoded RNA polymerase recognition sequence" includes any sequences recognized by one of the known phage-encoded polymerases and those undiscovered polymerases that have the identical functions of the known phage-encoded RNA polymerases.

"Polymerase primed sense product" and "Polymerase primed antisense product" refers to the strand of the amplification duplex strand which results from primer extension by the polymerase activity of either primer bound to the sense or antisense transcription product towards the 3' end and consists of in 5' to 3' direction an amplification primer, the copy of the target nucleic acid and a antisense sequence for subsequent binding of a second amplification primer.

"Single-stranded transcription product" are amplification intermediates and refers to products transcribed from either the intermediate duplex or the amplification duplexes. These products are co-polymers of both ribonucleotides and deoxyribonucleotides.

"DNA:RNA" duplex refers to a heteroduplex where one strand is DNA and the other strand is RNA.

"Target nucleic acid" refers to a nucleic acid sequence or subsequence of a larger nucleic acid (template) that is the object of repetitive copying.

"Template nucleic acid" refers to a nucleic acid which has within it a target nucleic acid subsequence which will be amplified by the process of this invention.

"Transcribe" refers to the polymerase activity during which an amplification duplex is used by a polymerase as a template for creating copies of the sense strand while leaving the amplification duplex unchanged.

"RNaseH" refers to an enzymatic activity that specifically digests the RNA strand of an RNA:DNA duplex.

A "Reverse Transcriptase that lacks RNAseH activity" or "RNaseH⁻ RT" is a reverse transcriptase that does not have any RNAse activity that can be measured using methods that are known in the art. Such reverse transcriptases can be purchased commercially.

"Wild Type RNA polymerase" refers to an RNA Polymerase (RNAP) which has not been mutated in any way that might affect the enzymatic activity or in any way alter promoter binding or substrate affinity or specificity.

A "phage-encoded RNA Polymerase" is a RNAP with 95% or more amino acid identity to a RNA Polymerase encoded by a bacteriophage gene. Phage-encoded RNA polymerases include, without limitation, a T3 RNA polymerase, a T7 RNA polymerase, and a SP6 RNA polymerase.

A "SP6 RNA Polymerase" is a RNAP encoded by a nucleic acid that is about 90% or more identical to GenBank Accession No. Y00105.

A "T7 RNA Polymerase" is a RNAP encoded by a nucleic acid that is about 90% or more identical to GenBank Accession No. M38308.

A "K11 RNA Polymerase" is a RNAP encoded by a nucleic acid that is about 90% or more identical to GenBank Accession No. X53238.

A "T3 RNA Polymerase" is a RNAP encoded by a nucleic acid that is about 90% or more identical to GenBank Accession No. X0298 1.

DETAILED DESCRIPTION

I. Introduction

The present invention provides methods and primers for copying intermediate duplexes and target nucleic acids. These methods involve the use of RNAPs, e.g., phage-encoded RNA polymerases, etc., which in part permit the amplification of nucleic acids. The uses of these methods are similar to those used for conventional nucleic acid amplification processes such as the ligase chain reaction and polymerase chain reaction technologies. Such uses include, without limitation, medical diagnostics, microorganism identification, generation of multiple copies of nucleic acid for subsequent cloning and recombination work and forensics.

The amplification method of this invention is distinct from the amplification systems described above, such as NASBA. The amplification products are a mixture of single- and double-stranded nucleic acids. The single strand nucleic acid products are typically polymers comprising ribonucleotides and deoxyribonucleotides. The double-stranded products consist of one strand of ribonucleotide/deoxyribonucleotide copolymer with at least one being pure DNA. The single-stranded transcription product is a particular advantage since detection of amplification may be performed using hybridization with detector oligonucleotides without denaturing the entire reaction mix. The presence of double-stranded DNA is an advantage if products are to be further manipulated using standard molecular biology techniques, for example, if the amplification products are to be cloned into a nucleic acid vector, e.g., a plasmid, a phagemid, etc. In addition, the single strand products are unmodified and contain copolymers of ribonucleotides and deoxyribonucleotides. Product accumulation can be logarithmic, with each transcription reaction yielding 10–100 copies rapidly providing high yields of product. This means that one copy of target nucleic acid will yield a million copies in 3 complete amplification cycles, assuming each step is 100% efficient. Since each cycle is generally completed in a minute or so, the production of millions of amplification products can be completed in just minutes. The reaction can be carried out in an isothermal manner. Increase specificity of the amplification methods can be obtained through the use of RNA polymerases that are thermally stable to temperatures as high as 50° C.

The methods of present invention do not require the presence of RNaseH activity, which is an advantage over methods such as NASBA. In a standard NASBA reaction, the RNA portion of the DNA/RNA heteroduplex intermediates are digested by RNaseH activity to render the DNA portion of the heteroduplex available for primer binding. When primers bind to RNA transcription products produced by the NASBA reaction, an RNaseH sensitive site is created which if digested results in dead-end truncated intermediates. Further RNAseH sensitive sites may be created by non-specific binding of oligonucleotides within the amplified transcripts again leading to dead-end truncated intermediates. The methods of the present invention, however, eliminate the need for the addition of the RNaseH activity and eliminate the production of truncated products making this technology able to amplify larger target segments than was previously possible.

In addition, the methods of the present invention are broadly applicable; i.e., it is not limited to any structural features of the template such as restriction enzyme sites. The methods are not limited by the length of the amplification product, since many RNA polymerases can transcribe large segments of DNA without falling off or pausing. Finally, the enzymes to be used in this reaction are highly stable, which simplifies the formulation of diagnostic kits.

Various components of the method and the methods themselves are described in more detail below.

II. Amplification Primers of the Present Invention

The choice of amplification primers will be dictated on the target for amplification. Preferably, the following criteria should be followed. The primers should be designed which will not cross-hybridize with each other taking into account the RNA polymerase binding site. In addition, the primers should be chosen which do not form secondary structures, again taking into account the RNA polymerase recognition sequence.

Preferably, the primer annealing temperatures should be at least 5° C. above the reaction temperature. Ideally, the primers should be in the range of 15 to 30 bases in length, however, it may be desirable to have shorter or longer recognition sequences. Also, the ability of the primers to bind may be affected by secondary structure of the template strands; secondary structure can prevent primer binding to the template and thus adversely affect the amplification yield. The easiest solution is to empirically scan the template strand with several primers whose target recognition sequences are displaced from each other by 2–5 bases. Usually regions can be found that effectively bind primers and which allow efficient amplification. Generally, the amplification primers are prepared synthetically by standard methods.

Typically, these oligonucleotide primers comprises sequences in the following order from 5' to 3': a RNA polymerase recognition sequence, a spacer sequence that consists of one nucleotide type or two different nucleotide types, and a target complementary sequence (TCS) which can bind a segment of a target nucleic acid, e.g., an intermediate duplex. These sequences may be adjacent to each other or separated by nonfunctional bases. Alternatively, two or more sequences may overlap each other. Each of these component sequences will be described in more detail below.

A. RNA Polymerase Recognition Sequences

RNA polymerases also have specific DNA sequences to which they bind which are referred to as promoter sequences (see e.g., Rong et al. (1998) *Proc. Natl. Acad. Sci., U.S.A.* 95: 515–519). Promoter sequences are generally in the range of 10 to 40 base pairs in length and have a specific sequence for each specific RNA polymerase. Therefore, the RNA polymerase for *E. coli* will only bind to the specific promoter sequence of *E. coli*. Minor variations in the promoter sequence affect the promoter strength, i.e., how well the promoter is utilized by the RNA polymerase. Therefore, a strong promoter directs a large number of initiation reactions and therefore more RNA product while a weak promoter directs fewer initiations and therefore less RNA product.

Often, when the minor promoter variants for a particular RNA polymerase are compared in both sequence and strength, a consensus promoter sequence can be derived which combines elements of all of the promoter sequences and leads to a "best" RNA polymerase promoter sequence. The structure of the RNA polymerase binding site will be dictated by the nature of the wild-type or mutant RNA polymerase being used. RNA polymerase recognition sequences are well-known in the art. Especially preferred recognition sequences are those for the phage-encoded RNAPs. Such sequences include, without limitation, TAATACGACTCACTATAGGGAGA (SEQ ID NO: 1) for T7 RNAP, ATTTAGGTGACACTATAGAAGAA (SEQ ID NO: 2) for SP6 RNAP, AATTAACCCTCACTAAAGG-GAGA (SEQ ID NO: 3) for T3 RNAP, and AATTAGGGCA-CACTATAGGGAGA (SEQ ID NO: 4) for K11 RNAP.

B. Spacer Sequence

The spacer sequence is a sequence of nucleotides that is juxtaposed between the target complementary sequence and the RNAP recognition sequence. The function of the spacer sequence is to assist the RNA polymerase to efficiently transcribe the templates of the invention. RNA polymerases are highly specific enzymes which generally require a fully double stranded DNA template and a functional promoter site to generate efficient synthesis of transcription products. It is possible under the certain conditions to obtain transcription products from RNA templates (see e.g., Arnaud-Barbe et al. (1998) *Nuc. Acids Res.* 26: 3550–3554). Under particular transcription conditions, a fully double stranded DNA template with a functional RNA polymerase recognition sequence can direct high levels of synthesis of single stranded RNA products. If the promoter (e.g., RNA polymerase recognition sequence) and its complement are DNA and are directly connected to a duplex in which bottom strand of the duplex is replaced with a complementary RNA strand, very little transcription product is obtained. That is, during transcription, if RNA polymerase attempts to move from the promoter directly to a lower RNA strand, little or no product is obtained. This is because the RNA polymerase is in the initiation complex conformation which is sensitive to the transcription conditions and can yield primarily very short abortive products. However, if a DNA spacer sequence of about 18 bases is positioned between the promoter and the region to be copied, the extra DNA length allows the polymerase to escape the initiation conformation to a elongation conformation which now is relatively insensitive to the nature of the template. Therefore, if a spacer sequence is inserted between the promoter and the region to be copied, the RNA polymerase may copy an RNA strand.

Essentially, the spacer sequence can be composed of any arrangement of up to two different nucleotide types. Thus, the spacer sequence can be composed of just one nucleotide, e.g., adenine, thymidine, guanosine, or cytosine. Ergo, in some embodiments, the spacer sequence is a homopolymer with the formula $(X)_n$, where n is from 12 to 20, and where X is selected from the group consisting of an adenine nucleotide, a guanine nucleotide, a cytosine nucleotide, and a thymidine nucleotide (SEQ ID NO:30. Examples of these spacer sequence embodiments include, without limitation, $(A)_{12-20}$ (SEQ ID NO: 5), $(T)_{12-20}$ (SEQ ID NO: 6), $(C)_{12-20}$ (SEQ ID NO: 7), and $(G)_{12-20}$ (SEQ ID NO: 8). In other embodiments, the spacer sequence is a combination of two different types of nucleotides, e.g., A and T, A and G, A and C, T and G, T and C, and G and C. For example, in certain embodiments, the spacer sequence comprises a nucleotide sequence having the formula $(XY)_n$, where n is preferably from 6 to 10 (SEQ ID NO:9). The nucleotides X and Y for these spacer sequence embodiments are independently selected from the group consisting of an adenine nucleotide, a guanine nucleotide, a cytosine nucleotide, and a thymidine nucleotide, and X and Y are not the same. In preferred embodiments, X is an adenine nucleotide and Y is a guanine nucleotide (SEQ ID NO:29).

Preferably, the length of the spacer sequence is from 8 to 30 nucleotides, even more preferably from 10 to 25 nucleotides, and still more preferably from 12 to 20 nucleotides, and most preferably 18 nucleotides. Thus, examples of spacer sequences include, without limitation, AAAGG-GAAGAGAGAGG (SEQ ID NO: 10), CTTTTTTTTCT-TCCC (SEQ ID NO: 11), GCGCCCGC (SEQ ID NO: 12), ATTTAATT (SEQ ID NO: 13), CAAACCCAA (SEQ ID NO: 14), etc.

C. Target Complementary Sequence (TCS)

The target complementary sequence (TCS) of an amplification primer is designed to bind to a segment of a target nucleic acid, e.g., an intermediate duplex. One of skill in art can readily design a TCS for a cognate nucleic acid sequence. The TCS should be of sufficient length and proper composition to be able to hybridize to a target nucleic acid using the methods of the present invention.

III. RNA Polymerases

RNA polymerases (RNAPs) are used in the methods of the present invention for, among other things, transcribing substrates in order to provide transcripts that are part of amplification cycle. Typically, RNAPs utilize ribonucleotides and cannot utilize deoxyribonucleotides. However, in the methods of the present invention, (e.g., the presence of Mn$^{++}$ and a mixture of rNTPs and dNTPs, etc.), the RNAPs incorporate ribo- and deoxyribonucleotides into transcripts. The RNAPs can be obtained from many sources, including from prokaryotes, phage, bacteriophage, eukaryotes, fungi, plants, archaebacteria, etc. The RNAPs should be stable and active under the conditions of the amplification methods.

In preferred embodiments, phage-encoded RNAPs are used. Examples of It phage-encoded RNAPs include, without limitation, a SP6 RNAP (e.g., GenBank Accession No. Y00105), a T7 RNAP (e.g., GenBank Accession No. M38308), a T3 RNAP (e.g., GenBank Accession No X02981), and a K11 RNAP (e.g., GenBank Accession No. X53238; (Dietz et al. (1990) *Mol. Gen. Genet.* 221: 283–286). These phagemid RNAPs have been cloned and expressed in bacteria and several are commercially available (e.g.,. SP6 RNAP, T7 RNAP, T3 RNAP). For example, the T7 RNAP (Davanloo et al. (1984) *Proc. Natl. Acad. Sci., U.S.A.* 81: 2035–2039) and the K11 RNAP (Han et al. (1999) *Protein Expr. Purif.* 16: 103–108) have been expressed as a soluble proteins in *E. coli*.

While it is generally preferable to use phage encoded polymerases in practicing this invention, other RNA polymerases should be able to be used by the reaction. The only requirement is that the promoter sequence be localized to a short segment of DNA that could be incorporated into an oligonucleotide primer. For example, the RNA polymerase promoter from *E. coli* is about 40 bases in length. One could use *E. coli* polymerase on one end of the amplicon and a phage promoter on the other. Some promoters have regulatory elements which control transcription by either enhancement or inhibition which may be useful for regulating amplification and the distribution of products.

IV. Mutant RNA Polymerases

In certain embodiments, RNAPs containing mutations as compared to the respective wild-type RNAP sequences are employed. These mutations permit, in whole or in part, the ability to incorporate dNTPs into a transcript (see e.g., Kostyuk et al. (1995) *FEBS Letters* 369: 165–168; Rusakova et al. (1998) *FEBS Letters* 423: 189–192). Examples of such mutant RNA polymerases include T7 polymerases that contain the following mutations Y639A, S641A, and Y639A/ S641A (Kostyuk et al. (1995)) as well as other polymerases with the equivalent residues that have been mutated. In order to use other mutant RNA polymerases, it is necessary first to identify the mutation that lends the ability of the RNA polymerase to utilize deoxyribonucleotides. This may be done first by comparing the active site of the known S641A mutant of T7 RNA polymerase which can incorporate dNTPs with the sequence desired RNA polymerase. Since the active sites of several RNA polymerases are known, homologies and other similarities may be identified which will identify the amino acid residue that needs to be changed. Any method for site directed mutagenesis may then be used to introduce the desired mutation into the RNA polymerase. For example, it is known that the consensus sequence among active sites of several RNA polymerases is Lys-Xaa-Xaa-Xaa-Xaa-Xaa-Xaa-Xaa-Tyr-Gly-Ser (SEQ ID NO: 15), where Xaa is any amino acid.

Another RNA polymerase, SP6 bears this exact active site sequence. It is predicted that changing the serine residue in this consensus sequence will allow for the construction of an SP6 polymerase with the ability to use deoxyribonucleotides rather than ribonucleotides, and yet maintain the promoter specificity of the natural SP6 RNA polymerase. When using a different RNA polymerase, the amplification reaction would be run in a similar manner to that described above except that the promoter sequence would match the specificity of the RNA polymerase being used. The use of different RNA polymerases may be an advantage in assays where it is desirable to amplify more than one gene. For example, if two genes are to be amplified from one mixture, and both utilize the mutant T7 RNA polymerase binding site, then there may be competition between the two amplification reactions. This may be minimized by utilizing a second RNA polymerase with a different promoter specificity for the second gene. Therefore, mutations that render a phage-encoded RNAP (e.g., a T7 RNA polymerase, a T4 RNA polymerase, a T3 RNA polymerase, a SP6 RNA polymerase and a K11 RNA polymerase) that is competent to incorporate dNTPs into a template nucleic acid can be constructed. In certain preferred embodiments, the mutant phage-encoded RNAP is a T7 RNA polymerase. The mutant T7 can contain one or more mutations. For example a T7 RNAP comprising a Y639F mutation, a S641A mutation, or a Y639F/S641A mutation can be employed.

V. RNaseH$^-$ Reverse Transcriptase

In the methods of the present invention, a reverse transcriptase lacking RNAse H activity is employed at several steps. Reverse transcriptases are enzymes that have the fundamental property of being able to efficiently copy RNA and creating a complementary DNA strand. Reverse Transcriptases in general require a single-stranded RNA or DNA target, a priming site such as a bound oligonucleotide, and absolutely require dNTPs as a substrate. From a single-stranded RNA strand with a bound primer, the product of a typical reverse transcriptase reaction will be double-stranded having the original RNA strand hybridized to the newly synthesized DNA strand. A common source of reverse transcriptase activity are certain retroviruses which carry an RNA genome. The reverse transcriptase activity is critical for these viruses since their RNA genomes must be converted into DNA in order to replicate.

One common reverse transcriptase is from avian myeloblastosis virus (commonly referred to AMV). This enzyme characteristically has an active reverse transcriptase activity and an associated activity which digests the RNA portion of the RNA/DNA hybrid product called RNaseH activity. For common molecular biology uses such as creating cDNA libraries after reverse transcribing cellular mRNAs, RNaseH activity can be detrimental since any primer binding site on the target RNA becomes a substrate for the RNaseH activity. This results in many truncated products and other incomplete products. AMV reverse transcriptase is used in the NASBA reaction which limits the size of amplified products that can be obtained. In contrast, another reverse transcriptase from moloney murine leukemia virus (MMLV) is finding more favor in molecular biology. This is because MMLV reverse transcriptase has a weaker intrinsic RNaseH activity resulting in less spurious cleavage of RNA/DNA hybrids allowing the synthesis of longer reverse transcriptase products in higher yield than was previously possible.

It has been found that MMLV reverse transcriptase consists of two domains, the catalytic domain and the RNaseH domain. Various investigators have mutated the RNaseH domain by deletion of short segments of the domain or by the introduction of certain point mutations. In either case, RNaseH activity is reduced to virtually non-detectable levels resulting in the ability of the resulting enzyme to create longer reverse transcription products in higher yields. Many of these enzymes are now commercially available from various sources and may either be of the deletion mutant or single base point mutation. Theoretically, it should be possible to use either form of the enzyme, but it is important that the enzyme be characterized as to residual RNaseH activity (Check with the manufacturer) as some commercial sources (depending on the mutation used) may have residual RNaseH activity.

Reverse Transcriptases generally prefer RNA as template strand for copying. However, a DNA template may be used as a template albeit not to the same extent as an RNA strand. However, some published data points to the ability of reverse transcriptase to utilize RNA/DNA copolymers as templates (Gudima et al. (1997) Nuc. Acids Res. 25: 4614–4618). While the binding affinity of reverse transcriptase for RNA and DNA can be one or two orders of magnitude different, the affinity for copolymers is somewhere between. In spite of this affinity difference, in fact under optimal conditions, reverse transcriptases can copy DNA strands efficiently, a fact that is exploited when reverse transcriptases are used for certain in vitro procedures such as creation of cDNA libraries. Since reverse transcriptase can use DNA efficiently as a template, and since the affinity of reverse transcriptase for copolymers is higher, then the amplification method presented in this application will not be limited by the use of copolymers as intermediates.

Reverse Transcriptase which is devoid of RNaseH activity is purchased from several commercial sources. Care should be taken in choosing the Reverse Transcriptase that has the no RNaseH activity since some manufacturers sell Reverse Transcriptases that have the RNaseH greatly reduced but not eliminated. Refer to the manufacturer specifications in order to choose the correct Reverse Transcriptase for use.

VI. Creation of Intermediate Duplexes

The methods of the present invention involve the amplification of intermediate duplexes. Intermediate duplexes typically comprise a double-stranded nucleic acid molecule. The double-stranded DNA molecule comprises a first and a second strand. The first strand contains an arrangement of sequences from 5' to 3': a RNA polymerase recognition sequence, a first spacer sequence comprising a sequence that consists of one nucleotide type or two different nucleotide types, and a first target complementary sequence which can bind to a segment of said target nucleic acid. The second strand comprises, from 5' to 3', a second target complementary sequence which can bind to a segment of said target nucleic acid, a second spacer sequence comprising a sequence that consists of one nucleotide type or two different nucleotide types, and a RNA polymerase recognition sequence. The target complementary sequences, spacer sequences, and RNA polymerase recognition sequences have been described above.

The intermediate duplex can be created by several methods. For example, FIG. 4 depicts an embodiment of how to produce an intermediate duplex from a double-stranded DNA target. In the first step, the double-stranded target, comprising an upper and a lower strand, is denatured by heating the sample above the melting temperature of the duplex to yield an upper and a lower strand. A first primer is then hybridized to the lower strand and extended by a Reverse Transcriptase, or another DNA polymerase such as Klenow polymerase, DNA polymerase I, T7 DNA polymerase, Taq Polymerase, or any other DNA polymerase activity. After the extension reaction, the newly synthesized strand, the first long strand, is separated from the template strand by heating. This is followed by annealing of the second primer and extension of the bound primer to form the intermediate duplex.

In other embodiments, the intermediate duplex can be formed from a double-stranded DNA target using a "bumper" oligonucleotide. FIG. 5 depicts an embodiment of such a method. In this embodiment, the double-stranded DNA target is heated to separate the upper and lower strands. A first primer (primer 1) is then hybridized to the lower strand to form a first primer-lower strand complex. This first primer-lower strand complex is then extended with a Reverse Transcriptase or with a DNA Polymerase to form a first long sense strand product-lower strand complex that has a 5' and a 3' end. Next, a bumper oligonucleotide is hybridized to a subsequence on the lower strand adjacent to the 5' end of the first sense strand product on the first sense strand product-lower strand complex; the bumper oligonucleotide binds to a sequence just upstream of either primer 1 or primer 2. The bumper oligonucleotide displaces the first sense strand product from the lower strand by extending the bumper oligonucleotide with a Reverse Transcriptase or with a DNA Polymerase. This permits the binding of a second primer (primer 2) to the first long strand sense and extension of primer 2 to form the intermediate duplex.

In still other embodiments, the intermediate duplex can be formed from an RNA target. FIG. 6 depicts an embodiment of such a method. First, the second primer (e.g., primer 2) is hybridized to a single-stranded target RNA molecule to form a second primer-RNA template complex. Then the second primer-RNA template complex is extended with a Reverse Transcriptase or a DNA Polymerase to form a first long antisense strand 25 product-template complex. The first long antisense strand product-RNA template complex is then denatured into a first long antisense strand product and the single-stranded RNA target molecule. The first primer is then hybridized to the first long antisense strand product to form a first primer-first long antisense strand product complex and the complex is extended with a Reverse Transcriptase or with a DNA Polymerase to yield the intermediate duplex [1].

In still other embodiments, an intermediate duplex is created from an RNA target molecule using a bumper oligonucleotide (see e.g., FIG. 7). The use of the bumper oligonucleotide allows the amplification reaction to be isothermal due to the lack of a need to have a heat denaturation step. As in the methods just described, the second primer is hybridized to a target RNA molecule to form a second primer-RNA template complex, which is extended with a Reverse Transcriptase or a DNA Polymerase to form a first long antisense strand product-template complex with a 5' and a 3' end. The first long antisense strand product is displaced from the target RNA molecule by hybridizing a bumper oligonucleotide to a subsequence on the target RNA molecule adjacent to said 5' end of the first sense strand product on the first sense strand product-lower strand complex. The bumper oligonucleotide is then extended with a Reverse Transcriptase or with a DNA Polymerase thereby displacing the first long antisense strand product. Then, the first primer is hybridized to the first long antisense strand product to form a first primer-first long antisense strand product complex, which in turn is extended with a Reverse Transcriptase or with a DNA Polymerase to yield the intermediate duplex.

VII. Nucleic Acid Sources for Creating Intermediate Duplexes

A variety of target nucleic acids can be used as starting materials for creating the intermediate duplexes. For example, the target nucleic acids may be DNA, genomic DNA, synthetic DNA, cDNA, RNA, tRNA, mRNA, or a combination of these nucleic acids. The nucleic acids can be obtained or purified from a variety of sources. For example, target DNA sequences may be a DNA isolated from a biological source, e.g., a bacterium, a cell, a plant, etc. Methods are known for lysing organisms and preparing extracts or purifying DNA. See, *Current Protocols in Molecular Biology* (Ausubel et al., eds., 1994)). One reliable method for the preparation of bacterial nucleic acid involves first treating the bacteria sample with lysozyme (final concentration 100 ug/ml) for 15 minutes to 1 hour at room temperature in TEN buffer (10 mM Tris pH 7.5, 10 mM EDTA, 50 mM NaCl). An equal volume of TENS is then added (TEN buffer+2% SDS) together with Proteinase K (final concentration 500 μg/ml). The sample is heated to 50° C. for 1 hour or as long as overnight. The samples are then extracted at least once with phenol:chloroform: Isoamyl alcohol (50:49:1). Sodium acetate is then added to a final concentration of 0.3 M from a 3 M stock solution pH 5.5. At least 2 volumes of 100% ethanol is then added and mixed well to precipitate the nucleic acid. The precipitate is spun at high speed in a microfuge for 5 minutes to pellet nucleic acids. The pellet is rinsed with 100% ethanol and dissolved in water.

Also, total RNA or polyA+ RNA can be reverse transcribed to produce cDNA which can serve as the target DNA. Alternatively, the target DNA sequences may be isolated using a variety of techniques. In general, the nucleic acid sequences encoding genes of the target DNA sequences of interest are cloned from cDNA and genomic DNA libraries by hybridization with a probe, or isolated using amplification techniques with oligonucleotide primers. Preferably, sequences from human pathogens, more preferably human sequences are used. For example, target DNA sequences are typically isolated from mammalian nucleic acid (genomic or cDNA) libraries by hybridizing with a nucleic acid probe, the sequence of which can be derived from the gene of the target DNA sequence being cloned.

Amplification techniques using primers can also be used to amplify and isolate, a nucleic acid encoding the target DNA sequence from DNA or RNA (see, e.g., Dieffenbach & Dveksler, (1995) *PCR Primer: A Laboratory Manual*). These primers can be used, e.g., to amplify either the full length sequence or a probe of one to several hundred nucleotides, which is then used to screen a mammalian library for the full-length nucleic acid of choice. For example, degenerate primer sets, can be used to isolate the relevant nucleic acids encoding the target DNA sequences. Nucleic acids can also be isolated from expression libraries using antibodies as probes. Such polyclonal or monoclonal antibodies can be raised using the predicted amino acid sequence of the target DNA sequence being cloned.

Polymorphic variants and alleles that are substantially identical to the gene of the target DNA sequence of choice can be isolated using nucleic acid probes, and oligonucleotides under stringent hybridization conditions, by screening libraries. Alternatively, expression libraries can be used to clone variant genes of the target DNA sequence being cloned such as, polymorphic variants, interspecies homologs, and alleles, by detecting expressed homologs immunologically with antisera or purified antibodies made against the predicated amino acid sequence of the target DNA sequence.

To make a cDNA library, one should choose a source that is rich in the mRNA of the target DNA sequence of interest. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, (1983) *Gene* 25:263–269; Sambrook et al., ($2^{nd}$ ed. 1989) *Molecular Cloning, A Laboratory Manual*; and Ausubel et al.

For a genomic library, the DNA is extracted from the tissue and either mechanically sheared or enzymatically digested to yield fragments of about 12–20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, (1977) *Science* 196:180–182. Colony hybridization is carried out as generally described in Grunstein et al., (1975) *Proc. Natl. Acad. Sci. USA*, 72:3961–3965.

An alternative method of isolating a nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. Degenerate oligonucleotides can be designed to amplify target DNA sequence homologs using the known sequences that encode the target DNA sequence. Restriction endonuclease sites can be incorporated into the primers. Polymerase chain reaction or other in vitro amplification methods may also be useful, for example, to clone nucleic acid sequences that code for the target DNA sequence proteins to be expressed. Genes amplified by the PCR reaction can be purified from agarose gels and cloned into an appropriate vector.

Synthetic oligonucleotides can be used to construct recombinant genes for use as probes or for expression of the target DNA sequence proteins. Oligonucleotides can be chemically synthesized according to the solid phase phosphoramidite triester method first described by Beaucage & Caruthers, (1981) *Tetrahedron Letts.* 22:1859–1862, using an automated synthesizer, as described in Van Devanter et al., (1984) *Nucleic Acids Res.* 12: 6159–6168. Purification of oligonucleotides is typically by either native acrylamide gel electrophoresis or by anion-exchange HPLC as described in Pearson & Reanier, (1983) *J. Chrom.* 255:137–149. The sequence of the cloned genes and synthetic oligonucleotides can be verified after cloning using, e.g., the chain termination method for sequencing double-stranded templates of Wallace et al., (1981) *Gene* 16:21–26. This method is performed using a series of overlapping oligonucleotides usually 40–120 bp in length, representing both the sense and non-sense strands of the gene. These DNA fragments are then annealed, ligated and cloned.

Alternatively, amplification techniques can be used with precise primers to amplify a specific subsequence of the target DNA sequence encoded by the nucleic acid. The specific subsequence is then ligated into a vector.

RNA target sequences that are used to create an intermediate duplex may be a single RNA target or different RNA targets. The RNA can be isolated as total RNA from a cell, bacterium, virus etc. See, Ausubel et al. The total RNA may be subsequently purified as poly A+ RNA or purified in a different manner to isolate certain species of interest. See Ausubel et al. Alternatively, the target RNA can be transcribed in vitro and used in the present invention.

VIII. Reaction Components

The following reaction components are also used in the methods that involve the amplification of intermediate duplexes.

Oligonucleotide Primers

The oligonucleotides that are used in the present invention (e.g., the first and second amplification primers) as well as oligonucleotides designed to detect amplification products can be chemically synthesized. These oligonucleotides can be labeled with radioisotopes, chemiluminescent moieties, or fluorescent moieties in a covalent or non-covalent manner. Such labels are useful for the characterization and detection of amplification products using the methods and compositions of the present invention.

Buffer

Buffers that may be employed are borate, phosphate, carbonate, barbital, Tris, etc. based buffers. See Rose et al., U.S. Pat. No. 5,508,178. The pH of the reaction should be maintained in the range of about 4.5 to about 9.5. See U.S. Pat. No. 5,508,178. The standard buffer used in amplification reactions is a Tris based buffer between 10 to 150 mM with a pH of around 7.5 to 8.8.

Salt Concentration

The concentration of salt present in the reaction can affect the ability of primers to anneal to the target nucleic acid. Potassium chloride can be added up to a concentration of about 50 mM to the reaction mixture to promote primer annealing. Sodium chloride can also be added to promote primer annealing.

Magnesium Ion Concentration

The concentration of magnesium ion in the reaction can be critical to amplifying the desired sequence(s). Primer annealing, strand denaturation, amplification specificity, primer-dimer formation, and enzyme activity are all examples of parameters that are affected by magnesium concentration. Amplification reactions should contain about from 2.5 to 30 mM magnesium concentration excess over the concentration of dNTPs. The presence of magnesium chelators in the reaction can affect the optimal magnesium concentration. Those of skill in the art, can readily carry out a series of amplification reactions over a range of magnesium concentrations to determine the optimal magnesium concentration. The optimal magnesium concentration can vary depending on the nature of the target nucleic acid(s) and the primers being used, among other parameters.

Manganese Ion Concentration

The presence of manganese ions is required for several steps in the methods of the present invention. These steps typically involve the transcription of a substrate with a RNA polymerase in order to incorporate dNTPs. For example, such steps involve the transcription of the intermediate duplex with an RNA Polymerase, the transcription of the first amplification duplex with an RNA polymerase, and the transcription of the second amplification duplex with an RNA polymerase. The manganese ions are typically provided in the form of a salt, e.g., manganese chloride. In preferred embodiments, the $Mn^{++}$ is present in a concentration of between 1 μM to 30 mM. In more preferred embodiments, the $Mn^{++}$ is present in a concentration of between 10 μM to 20 mM. In still a more preferred embodiment, the concentration of manganese ion is 10 mM. One of skill in the art can optimize the manganese ion concentration for a particular set of reaction conditions and substrates.

Deoxyribonucleotide Triphosphate Concentration

Deoxyribonucleotide triphosphates (dNTPs) are added to the reaction to a final concentration of about 200 μM to about 5 mM. Each of the four dNTPs (G, A, C, T) should be present at equivalent concentrations. The dNTPs can be prepared from commercially available stock solutions or from dry powder stocks of each dNTP.

Ribonucleotide Triphosphate Concentration

Ribonucleotide triphosphates (rNTPs) are added to the reaction to a final concentration of about 200 μM to about 5 mM. Only the rNTP(s) that are represented in a spacer sequence are present in the reaction. For example, if the spacer sequence contains adenine and guanosine, then rATP and rGTP should be present in the reaction. Similarly, if only adenine is present in a spacer sequence, then rATP should be present in the reaction.

Other Agents

Stabilizing agents such as gelatin, bovine serum albumin, and non-ionic detergents (e.g. Tween-20) can be added to amplification reactions.

Examples of Reaction Conditions

The reaction conditions for amplification are optimized to allow efficient incorporation of both dNTPs and rNTPs by the RNA polymerase. These conditions include 0.1M Tris-acetate pH 8.0 or within a range of pH 7.0 to pH 8.5, magnesium in the range of 2.5 to 30 mM to balance out the nucleotides present in the reaction, dNTPs at a concentration of 200 uM to 5 mM, and rNTPs at a concentration of 200 uM to 5 mM, and manganese at a concentration of 1 uM to 30 mM.

A typical reaction buffer may be performed as follows. A 5× Reaction Buffer is prepared which contains 0.2M Tris-acetate pH 8.0, 10 mM Mg acetate, 20 mM spermidine acetate, 0.25% Tween 20, 25 mM DTT. Thus, a 1× Reaction buffer would typically be the final concentration of the buffer in the amplification methods.

IX. Reaction Temperature

The temperature of the reaction mixture for the amplification of the intermediate duplex can vary over the range at which the enzymes in the mixture are active and products are produced. However, the methods can be carried out at a single temperature, e.g., isothermally. For example, the methods can be carried out at a single temperature of between 25° C. and 55° C., or at a single temperature of greater than 50° C. up to the thermal stability limit of the enzymes involved in the amplification reaction.

X. Amplification of an Intermediate Duplex

The methods of the present invention may be carried out in a discontinuous manner. That is, one or more of the amplification steps can be performed separately and the product used as the basis of the next step. In preferred embodiments, however, the amplification of the intermediate duplex is carried out in a single reaction vessel. Thus, typically in a single reaction vessel the reaction buffer, the intermediate duplex, the enzymes, (e.g., RNAP, RNaseH⁻ RT, etc), amplification primers are combined in an aqueous solution. Preferably, the reaction can be carried out in a thermal cycler to facilitate incubation times at one or desired temperatures.

The starting point of the reaction is called for purposes of description the intermediate duplex. Examples of intermediate duplexes are shown as [1] in FIGS. 1, 4–7 An embodiment of the cyclic amplification reaction is outlined in FIG. 1. Detailed drawings of embodiments of the each half of the amplification cycle are presented in FIGS. 2 and 3. The intermediate duplexes are formed either synthetically, in practical use by any of the means described herein, or using methods known to those of skill in the art. The intermediate duplex has a complete double-stranded copy of the RNA polymerase binding site followed by the sequence to be amplified and will be blunt-ended directly after the second primer binding site. In another composition, intermediate will contain an incomplete second polymerase binding site that is unpaired to its complement.

In the first step of the amplification reaction, the RNA polymerase will bind to a RNA polymerase recognition sequence and in the presence of dNTPs, and the rNTPs represented in the spacer sequence(s), manganese and magnesium, transcribe the intermediate duplex to create single strands labeled the sense transcription product. This product does not contain the RNA polymerase binding site since the RNA polymerase does not make a copy of the promoter. In addition, the single-stranded products will be copolymers of both dNTPs and the rNTPs present in the reaction mix. Also, since this is a transcription reaction, incorporation of primer is not directly necessary to produce these intermediate products.

The single-stranded products are then free to bind primer 2 (see e.g., [3] in FIG. 1 and 3). While RNA polymerases may extend bound primers, it is more efficient to have a second polymerase activity, preferably a reverse transcriptase lacking RNaseH activity which will efficiently extend primer 2 across the amplified region. The sense transcription product will also be extended across the RNA polymerase promoter which renders it active to bind the mutant RNA polymerase. This product is called Amplification Duplex 2 (see e.g., [4] in FIGS. 1 and 4).

FIG. 2 shows in detail how an embodiment of the reaction works with a spacer region within the promoter. The first line in the figure shows a typical amplification primer with an example of a spacer region consisting of alternating A's and G's. The primer, which is DNA, will bind to the sense transcription product. The sense transcription product has a complementary sequence consisting of alternating T's and C's. Since there is no rU nor rC in the system, the combination of the reaction conditions with the use of the mutant RNA polymerase leads to efficient incorporation of dT and dC in the transcription process. Therefore, binding of primer 2 to the sense transcription product leads the formation of a functional RNA polymerase promoter together with an 18 base DNA extension (contributed by the primer). The bound primer 2 is then extended by the Reverse Transcriptase activity to complete formation of amplification duplex 1.

Thus, for the primers depicted in FIG. 2, the transcription of amplification duplex 1 results in the formation of a transcript that is a mixed polymer of dNTPs and rATP and rGTP. The 3' tail of this transcript will only contain dC and dT. Referring back to FIG. 1, the RNA polymerase will transcribe the Amplification Duplex 1 to produce the antisense transcription product [5] that is free to bind to primer 1 [6].

Then, primer 1 is extended across the target sequence. As before, the antisense transcription product is also extended across the RNA polymerase binding site to yield amplification duplex 2 [7]. Amplification Duplex 2 is transcribed by the mutant RNA polymerase to produce the sense strand transcription product [2]. Further rounds of amplification will then occur following the same mechanism.

Referring to FIG. 3 for specific details, the antisense transcription product from FIG. 2 binds to primer 1 again with the spacer sequences complementing each other and leading to an all DNA promoter sequence with an all DNA spacer region. Extension of the primer and the 3' end of the antisense product results in the production of amplification duplex 2. Amplification Duplex 2 can then be transcribed by the RNA polymerase to yield the sense transcription product which is a copolymer of dNTPs and rATP and rGTP. The most 3' segment of this transcript is a DNA segment consisting of dC and dT. The cycle continues by performing the steps in FIG. 2 and then FIG. 3 repetitively until some reaction component becomes exhausted.

XI. Detection of the Amplification Products

Those of skill in the art will recognize that there are many ways to detect nucleic acids. The following are examples of methods used to detect nucleic acids that are present in the amplification reactions of the present invention. The methods of the present invention can involve detecting such amplification products as the antisense transcription product, the first amplification duplex, or the second amplification duplex. These products may be detected by the use of oligonucleotides that are labeled with a detectable moiety and are incorporated into a reaction product. Alternatively, amplification products can be detected by hybridizing a detection oligonucleotide comprising a detectable moiety to an amplification product. The presence of a detectable moiety can be ascertained using appropriate means, e.g., visual means for detectable moieties producing a visible signal, a fluorometer for fluorescent labels, a spectrophotometer for labels of the visible light range, a scintillation counter for radioactive labels, etc. In addition, the following methods, as well as other methods known in the art, may be used to detect amplification products of the present invention.

A. Ethidium Bromide Staining

The method of using ethidium bromide, and other nucleic acid binding labels, to detect nucleic acids in agarose gels is well known in the art. See, e.g., Ausubel et al. Briefly, the amplification products can be electrophoresed on an agarose gel. The agarose gel is then incubated with the intercalating agent, ethidium bromide. The ethidium bromide soaked gel can then be illuminated with ultraviolet light. The ethidium bromide fluoresces under ultraviolet light and permits the visualization of DNA bands in the gel. The molecular size of the product can be estimated by co-electrophoresing a sample with known molecular sizes of DNA, a "DNA ladder." Such DNA ladders are available from a variety of commercial vendors.

B. Fluorescence Resonance Energy Transfer

Methods employing the technique of fluorescence resonance energy transfer (FRET) can be employed using the methods and compositions of the present invention. FRET is a distance-dependent interaction between a donor and acceptor molecule. The donor and acceptor molecules are fluorophores. If the fluorophores have excitation and emission spectra that overlap, then in close proximity (typically around 10–100 angstroms) the excitation of the donor fluorophore is transferred to the acceptor fluorophore.

Hairpin FRET Assay

In one particular method employing FRET, fluorescent energy transfer labels are incorporated into a primer that can adopt a hairpin structure. See Nazarenko et al., U.S. Pat. No. 5,866,336; Nadeau et al., U.S. Pat. No. 5,958,700; Tyagi et al., U.S. Pat. No. 5,925, 517. The primers can be designed in such a manner that only when the primer adopts a linear structure, i.e., is incorporated into an amplification product, is a fluorescent signal generated. See Nazarenko et al., U.S. Pat. No. 5,866,336; Nadeau et al., U.S. Pat. No. 5,958,700.

In accordance with the method of U.S. Pat. No. 5,866, 336, FRET pairs can be incorporated into the primers of the present invention or into signal oligonucleotides that can be added to the reaction mix, to afford a method of detecting the incorporation of the primer into a polymerization product. The primers of the present invention or the oligonucleotides are able to adopt an intramolecularly base-paired structure (e.g., a hairpin structure). The signal oligonucleotide or the primers of the present invention are modified with two fluorescent dye moieties that form a donor/acceptor dye pair. For example, the donor dye moiety can be fluorescein or a fluorescein derivative and the acceptor can be DABCYL. The two dyes are positioned on the labeled oligonucleotide such that they are in close spatial proximity (typically around 10–100 angstroms) in the base-paired, folded secondary structure. If the dyes are in close spatial proximity then the donor fluorescence is quenched by the acceptor dye.

The signal oligonucleotide or primer comprise a single-stranded target binding sequence and an intramolecularly base-paired secondary structure 5' to the target binding sequence. At least a portion of the target binding sequence forms a single-stranded tail which is available for hybridization to the middle of the amplified target sequence, the signal oligonucleotide having linked thereto a first dye and a second dye such that fluorescence of the first or second dye is quenched. The annealed signal oligonucleotide is extended to produce a signal oligonucleotide extension product. After denaturation, a primer is annealed to the signal oligonucleotide extension product and extended. This linearizes or unfolds the secondary structure and producing a change in a fluorescence parameter. The change in a fluorescence parameter is an indication of amplification of a desired sequence. Those of skill in the art will recognize a variety of FRET pairs that can achieve the desired results.

TaqMan Assay

The amplification products can be detected in solution using a fluorogenic 5' nuclease assay-The TaqMan assay. See Holland et al., (1991) *Proc. Natl. Acad. Sci., U.S.A.* 88: 7276–7280; Livak et al. U.S. Pat. Nos. 5,538,848, 5,723, 591, and 5,876,930. The TaqMan probe is designed to hybridize to a sequence within an amplification product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. The excising of the 5' fluorophore results in an increase in fluorescence which can be detected.

A TaqMan probe can be used in conjunction with the present invention. For example, a primer that is labeled with the an appropriate donor/quencher pair and is complementary to a portion of the target nucleic acid sequence between where the target-specific primers bind, can function in the TaqMan assay.

XII. Kits

The practice of this invention may be made more convenient by the using a kit format. The kit may contain all of the components necessary to practice the invention together with detailed instructions. For example, a kit may contain a vial of the mutant RNA polymerase, a vial of a reverse transcriptase activity which is devoid of RNaseH activity, a dNTP mix, a mix of rATP and rGTP, an optimized reaction buffer, control primers and template so the user may determine the efficiency of amplification. The user would supply specific primers for the application and template nucleic acids. A detailed set of instructions would include selection criteria for the preparation of primers, suggestions for template preparation, and detailed instructions on how to practice the invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are offered to illustrate, but not to limit the claimed invention.

Example 1

Purification of Mutant RNA Polymerase

T7 Mutant RNA polymerase is prepared from cells carrying a plasmid containing the whole mutant T7 TNA polymerase situated behind a strong bacterial promoter sequence (The trp promoter). Over-expression occurs when the cells are treated with tryptophan. Mutant T7 RNA polymerase is prepared by standard chromatographic procedures and stored frozen in aliquots at −20° C.

A modified and simplified procedure for purification of T7 RNA polymerase is as follows. Medium for growing the cells must have little or no tryptophan to minimize ED expression of the cloned gene. First, a saturated overnight culture is prepared in ACH/M9 medium (A minimal medium containing 2% Acid Casein Hydrolysate in 1× M9 Salts. Acid casein hydrolysate and powdered M9 salts are available commercially from several sources such as Sigma Chemical, St. Louis.). The saturated overnight culture is diluted 1:10 into 2 liter flasks, each of which contains 1 liter of ACH/M9 medium with 100 ug/ml ampicillin. The flasks are shaken and maintained at 30° C. for 4 hours at which time tryptophan is added to 100 μg/ml. Temperature is maintained at 30° C. and the cells are shaken for an additional 2 hours. Cells are harvested by centrifugation and stored at −70° C. Total yield of cells is about 2.5 g per liter of medium.

T7 RNA polymerase is readily degraded by a protease which is present in the cell membrane called OmpT protease. This protease has the properties that it is expressed in many strains of *E. coli* at higher temperatures, and that it is released from the cell membrane using detergent lysis of the cells. Therefore, to minimize ompT proteolysis, the cells are not grown at any point at 37 C, nor is there any detergent used in the lysis procedure.

The cell pellet was frozen in 20 ml lysis buffer. Purification is initiated by thawing the cells at room temperature. The lysis buffer is made of 25 ml of Buffer C (20 mM Tris-Cl, pH 8.0, 1 mM EDTA, 1 mM DTT, 5% glycerol) which is added together with 20 mg of lysozyme, 200 μl phenylmethylsulfonyl chloride (20 mg/ml in isopropanol), and 100 μl leupeptin (Sigma; 5 mg/ml in water). Mix the solution well and incubate at 4° C. for 45 minutes. Cells are lysed by repeated freeze/thaw cycles. The cell suspension is mixed and frozen at −80° C. for 30 minutes. The suspension is then thawed and refrozen at −80° C. Then, thaw the suspension at room temperature resulting in a highly viscous suspension.

Place the suspension in a blender and blend in several short bursts until the suspension is uniformly liquefied. Spin the suspension at 5400 RPM for 20 minutes to pellet the cell debris. Dilute the suspension to 45 ml and add 5 ml 10% polymin P dropwise. After stirring for 20 minutes, pellet the precipitated nucleic acids for 20 minutes at 5400 RPM. To the supernatant, add 35g solid ammonium sulfate per 100 ml of lysate. Stir the suspension at 4° C. to precipitate the protein at 4° C. for at least 20 minutes or overnight. Spin out the precipitate at 12.5 K for 20 minutes. Decant the supernatant and drain the pellets well. Add Buffer C to dissolve the pellets, and spin out any insoluble material at 12.5 K for 20 minutes.

Check the conductivity of the suspension and adjust with Buffer C so that it is close to that of Buffer C+50 mM NaCl. Load the sample onto a 20 ml column of SP Sepharose. Wash the column with Buffer C+50 mM NaCl until the $OD_{280}$ comes down to 20 baseline. Elute the bound protein with Buffer C+0.2 M NaCl. One major protein peak containing the mutant RNA polymerase is eluted. Read the $OD_{280}$ of each fraction and combine the peak fractions.

Load these directly onto a 5 ml Cibacron Blue column equilibrated in Buffer C. Wash the column with Buffer C+0.5M NaCl which removes some contaminating proteins while the mutant polymerase remains tightly bound.

Elute the mutant polymerase with Buffer C+2 M NaCl. Collect 2 ml fractions and read the $OD_{280}$ of each fraction. Pool the major peak fraction and dialyze into Buffer C+100 mM NaCl+50% glycerol. The concentration of the enzyme is determined from it's absorbance at 280 nm using a molar extinction coefficient of $1.4 \times 10-5$ M-1 cm-1. Store in aliquots at $-20°$ C.

To assess the activity of the purified protein, a simple transcription assay may be run as follows. Prepare a 5×transcription buffer by mixing 200 µl of 1M TrisAcetate pH 8.0, 25 µl of 1M DTT, 1-µl of 0.5M EDTA, 40 µl of 1M Spermidine, 25 µl of 25% Tween, and 0.7 ml of water. The reaction is set up by mixing 2 µl of 5× buffer, 4 µl of 10 mM dNTPs or rNTPs, either 1 µl of 150 mM $MnCl_2$ or 1 µl of 100 mM $MgCl_2$, 100–500 ng of template containing the T7 promoter, and water to 9 µl. Then, 1 µl of diluted polymerase is added and the reaction incubated for 1–2 hours. The products are run on a 2% agarose gel in 1×TAE at 75V–100V until done. The products are visualized using ethidium bromide.

Example 2

Detailed Description of the Amplification Procedure

Stock Solutions: All stock solutions are prepared using deionized water. Where appropriate, stock solutions are autoclaved to maintain sterility of the solutions.

The following stock solutions are required: 1M Tris-acetate pH 8.3, 1M potassium acetate; 1M magnesium acetate, 1M $MnCl_2$; 10% Tween, 0.5M Spermidine-3HCl, 1M DTT.

5× Amplification Buffer: Mix 0.575 ml of deionized water, 0.2 ml of 1M Tris-acetate pH 8.3, 0.05 ml of 1M magnesium acetate, 0.1 ml of 1M potassium acetate, 0.025 ml of 1M spermidine trihydrochloride, 0.025 ml 1M dithiothreitol, and 0.025 ml of 10% (v/v) of Tween-20. Larger quantities of amplification ma be prepared and aliquoted and then stored at $-20°$ C.

In a separate tube, mix 0.05 ml of 1M $MnCl_2$ with 0.95 ml of water for a 50 mM stock solution. Prepare this fresh each day.

A combined mix of all four dNTPs can be purchased from many suppliers. Concentrations of 10 mM and 100 mM with respect to each dNTP are available. The stock solution needed for amplification is 10 mM, so that the 100 mM stock should be diluted 1:10 in 10 mM Tris-Cl pH 7.5.

rATP and rGTP are purchased as pre-prepared stock solutions from various suppliers.

Oligonucleotides including amplification primers and signal probes are synthesized by several commercial services. Primers are cartridge purified. All primers are dissolved in either water or 10 mM Tris-Cl pH 7.5, 1 mM EDTA at a concentration of 100 µM.

Both wild type RNA polymerase and RNaseH depleted Reverse Transcriptase (Moloney) can be purchased from various commercial sources. It is imperative to purchase the RNaseH- variant of Reverse Transcriptase since RNAse activity can digest all intermediates and stop the amplification reaction.

A synthetic template which has a T7 promoter at the 5' end and is blunt ended on the 3' end for use in these studies is produced using PCR as follows. T7 whole genomic DNA is purchased from Sigma Corp. at a concentration of 0.5 mg/ml. Dilute an aliquot of T7 DNA 1:10 in water for the PCR reaction.

Set-up 4 or more PCR tubes, each containing 10 µl of 10×PCR buffer, 2 µl of 10 mM dNTPS, 1 µl each of AMP010 and AMP012, 1 µl of T7 DNA as prepared above, 84 µl of water, and 1 µl of Taq Polymerase (0.2 U/ul). Cover each reaction with 80–100 µl of mineral oil, and seal the tubes. Place in a thermocycler and amplify using the following heating/cooling profile: 1 minute at 94° C., 1 minute at 55° C. and 1 minute at 72° C. for 30 cycles. Then, finish with a 5 minute incubation at 72° C.

Remove oil from reaction by adding 100 µl chloroform, mixing gently, then allowing the upper and lower phases to form again and withdraw the aqueous phase (usually forming a bubble within the chloroform layer). Combine all aqueous phases and extract once with an equal volume of phenol:chloroform:isoamyl alcohol (50:49:1). The next step is used to purify the amplicon away from excess primers and nucleotides and salts using ultrafiltration. Remove the aqueous layer from the phenol layer and place into a Centrex UF-0.5 100K MWCO spin column (Schleicher and Schuell). These are small microcentrifuge compatible filter/tube devices that separate components by ultrafiltration through a filter with a defined molecular weight cut-off. For a standard PCR reaction, the size of the ultrafilter depends on the size of the amplicon. A 100K MWCO filter will remove effectively primers, nucleotides, and salts while retaining the amplicon in the upper chamber over the filter. Samples are centrifuged at 5K RPM in a standard microfuge for 5–10 minutes. The retentate in the filter will only be a few microliters. Wash the retentate twice with 10 mM Tris pH 7.5 twice by adding the wash and spinning again at 5K for 5–10 minutes. To the retentate, add about 50–100 µl of 10 mM Tris pH 7.5, invert the filter over a fresh tube and spin at 5K for 2–3 minutes. Add an additional 50–100 µl of 10 mM Tris pH 7.5, invert the filter, and spin for 2–3 minutes to rinse the filter off. Combine these two washes and calculate the concentration of amplicon by measuring the A260 of a dilution of the amplicon, then applying the formula: Concentration (µg/ml)=A260×dilution factor×50.

The following is the complete sequence of the amplicon used as a model template (SEQ ID NO: 26) for these studies extracted from GenBank (Accession number g216011) starting at residue 259 and ending at residue 581. The position of the AmpSig5 signal sequence is one base pair downstream of the Amp010 primer and is indicated by a box. Primers are in capital letters.

```
                        259
AMP010 -→      Spacer        ⫯
AATTTAATACGACTCACTATAGGGAGAGAGAGAGAGAGA|C|TCCTAAAGT
```

```
TTAAATTATGCTGAGTGATATCCCTCTCTCTCTCTCT|G|AGGATTTCA

AMPSig5
CACCTCCTAACGtagcctacacctaaaga
GTGGAGGATTGCatcggatgtggatttct cccatcaagtcaacgcctatcttaaagtttaaacataaagaccagaccta
gggtagttcagttgcggatagaatttcaaatttgtatttctggtctggat aagaccagacctaaagacactacataaagaccagacctaaagacgccttg
ttctggtctggatttctgtgatgtatttctggtctggatttctgcggaac ttgttagccataaagtgataaccttttaatcattgtctttattaataacaac
aacaatcggtatttcactattggaaattagtaacagaaataattatgttg tcactataaggagagacaacttaaagagacttaaaagattaatttaaaat
agtgatattcctctctgttgaatttctctgaattttctaattaaatttta ttatcaaaaagagtattgacttaaagtctaacctataggatacttacagc
aatagttttctcataactgaatttcagattggatatcctatgaatgtcg catcGAGAGGGACACGGCGAATAGC 581
gtagCTCTCCCTGTGCCGCTTATCG
       ←- AMP012
```

The amplification reaction is run in 20 μl as follows: Mix 4 μl 5× amplification buffer, 2 μl each of 10 mM dNTPs, 10 mM rATP, and 10 mM rGTP, 1 μl each of primer 1 and primer 2, 2 μl of 50 mM MnCl₂, 3 μl of water, and 1 μl of template.

Prepare enough master mix for the number of samples plus 1 or 2 extra reaction to help compensate for pipetor reaction and the detergent content of the master mix.

For double-stranded DNA targets, heat the reaction mix to 94° C. for 2 minutes. Place the tubes immediately in a 42° C. bath for 2 minutes. For RNA targets, it is only necessary to warm the reaction mixtures to about 65° C., then cool to 42° C. Then add 1 μl (up to 50 activity units) of mutant T7 RNA polymerase and 1 μl (30 units) of RNaseH⁻ reverse Transcriptase. Incubate for 1 hour at 42° C.

Run products on agarose gels, or analyze by hybridization analysis such as slot blotting using AmpSig-5 as a signal probe.

TABLE 1

Oligonucleotides Used in this Work

| Designator | Pos. in T7 | Use in this work | Sequence | SEQ ID NO. |
|---|---|---|---|---|
| AMP010 | 259 | Amplification Primer | AATTTAATACGACTCACTATAGGGAGAGAGAGAGAGACTCCTAAAGTCACTCCTAACG | 16 |
| AMP011 | 581 | Amplification Primer | AATTTAATACGACTCACTATAGGGAGAGAGAGAGAGAGCTATTCGCCGTGTCCCTCTCG | 17 |
| AMP011S | 581 | Amplification Primer | AATTTAATACGACTCACTATAGGGAGAAGGAGAAAAAGAGCTATTCGCCGTGTCCCTCTCG | 18 |
| AMP012 | 581 | PCR Primer | GCTATTCGCCGTGTCCCTCTCG | 19 |
| AMP013 | 259 | PCR Primer | CTCCTAAAGTCACTCCTAACG | 20 |
| Bump003 | | Bumper | CTGTGTCCCTATCTGTTACA | 21 |
| AMPSig5-B | 282 | Signal Oligonucleotide | CCATCCTAAAGCCAACACCTAA | 22 |
| AMPSig5-AS-B | 282 | Signal Oligonucleotide | TTAGGTGTTGGCTTTAGGATGG | 23 |

(T7 Promoter) = AATTTAATACGACTCACTATAGGGAGAGAGAGAGAGA (SEQ ID NO:24)
(T7 Promoter S) = AATTTAATACGACTCACTATAGGGAGAAGGAGAAAAAGA (SEQ ID NO:25)

Example 3

Amplification Results by Gel Analysis

Agarose Gel Electrophoresis analysis of amplification reactions allows direct visualization of products including template (which should increase in intensity as the amplification reaction proceeds, and single strand transcripts (which should migrate with a faster mobility than the template). The amount of transcripts too should increase in intensity when stained with ethidium bromide. Reaction mixtures are prepared by mixing the following: 4μl 5× Amplification Buffer, 2 μl 10 mM dNTPs, 2 μl 10 mM rATP, 2 μl 10 mM rGTP, 1 μl 100 μM Amp010, 1 μl 100 μM Amp011, 2 μl 25 μl MnCl₂, and 3 μl water. To each tube 1 μl of template is added, except one tube which will serve as a no template control. The template is a PCR product from T7 genomic DNA amplified using Amp010 and Amp012 as primers and purified by ultrafiltration. Enough reaction mix was prepared for 7 reactions, and 18 μl of mix was aliquoted into fresh tubes. Tubes were then warmed to 42° C. in a water bath for at least 2 minutes at which point 1 μl of mutant T7 RNA polymerase was added. The amount of reverse transcriptase added was titrated by serially diluting a sample of reverse transcriptase (RNaseH-; Life Technologies) with 10 mM TrisAc pH 8.3 to 200 units/μl, 100 units/μl, and 50 units/μl. One microliter was added to each tube of the titration series and the reactions were incubated at 42° C. for 1 hour. When done, 4 μl of a dye solution was added (0.025% bromophenol blue and 0.025% of xylene cyanol in water). A 2% agarose gel containing 2 μl/ml of ethidium bromide was poured and allowed to harden at room temperature. A 6 μl of each reaction was then loaded and the gel run at 100V for about 45 minutes or longer until the bromophenol blue was around ¾ of the way through the gel. The gel was then photographed under UV light.

The data is presented FIG. 8. The very first lane is the 1 Kb ladder (Life Technologies) for size markers. The second lane is the input template for the amplification giving a reference for comparison to the amplification reactions. The third lane shows the results of a transcription reaction using T7 Mutant RNA polymerase only. The lane shows the original template band plus a light transcript band below the template. The amount of transcript synthesized appears low, but this is only because $\frac{1}{10}^{th}$ of the reaction is loaded into this lane. Lane 4 is negative control in which a complete reaction is constructed without added template and which shows that some low molecular weight non-specific products are created by the action of the 2 enzymes in the reaction. Lane 5 through 7 are complete amplification reactions in which 50, 100, and 200 units of reverse transcriptase was added. The reaction products consist of double strand template and single strand transcripts. A high brightness view is shown in FIG. 8A so that the intensity of the input template can be compared to both the transcription and amplification reactions. A higher contrast view of the same gel is presented in FIG. 8B which now makes the template band invisible, but which more clearly shows the nature of the amplification products. Comparing the differences in products between 50, 100, and 200 units of reverse transcriptase reveals that the higher reverse transcriptase levels do not increase the amount of product obtained from the amplification.

Gel analysis of amplification products usually display expected products of an increased intensity of the template and a very strong intensity for transcripts. Generally, the product distribution should include an increase in the intensity of a band having the same or roughly the same mobility of the input template, and a second band with a higher mobility representing single strand intermediates. There may be one additional band of a mobility close to that of the template which would represent hybridized upper and lower transcription products. The template band is less apparent in this view, but the increase in the amount of template and transcript can be more easily seen. In view of the fact that the pattern is as expected, and that the amount of both template and transcript are visibly more intense after amplification in a view of the gel in which the template band nor transcription products are not visible indicates that a significant amount of amplification was obtained.

Example 4

Hybridization Analysis of an Isothermal Amplification Reaction

Hybridization analysis is a method that confirms what an how much of a particular product is being produced. Unlike agarose gel electrophoresis, hybridization analysis identifies objectively the nature of the products based on binding of a signal oligonucleotide to a sequence contained within the amplified product. Two biotinylated signal oligonucleotides were synthesized for this analysis, AmpSig5-B, and AmpSig5AS-B. AmpSig5 is the same sense as in the upper strand of the template so it can only bind to single strand products derived from the lower strand. AmpSig5AS-B is an exact complement of AmpSig5-B and is the same sense as the lower strand of the template. Therefore, it will bind only to transcription products derived from the upper strand. Since the first step of the reaction is transcription from the upper strand of the template, AmpSig5AS-B should bind to and give a signal from the transcription products while AmpSig5-B will not. If AmpSig5-B is used as a probe in this system, then a positive reaction should be obtained only if at least one round of cycling has occurred.

To examine an amplification reaction by hybridization analysis, first an amplification reaction was run by preparing a reaction mix containing the following components: 4 µl 5× Amplification Buffer, 2 µl 10 mM dNTPs, 2 µl 10 mM rATP, 2 µl 10 mM rGTP, 1 µl 100 µM Amp010, 1 µl 100 µM Amp011, 2 µl 25 µl $MnCl_2$, 3 µl water, and 1 µl of template. The template is a PCR product from T7 genomic DNA amplified using Amp010 and Amp012 as primers and purified by ultrafiltration. Enough reaction mix was prepared for 10 reactions, and 18 µl of mix was aliquoted into fresh tubes. Tubes were then warmed to 42° C. in a water bath for a at least 2 minutes at which point 1 µl of mutant T7 RNA polymerase was added. As controls for this experiment, tubes containing only T7 (without reverse transcriptase) and with reverse transcriptase only (no T7 mutant polymerase), along with a tube with no enzymes to measure signal from the template. In addition, an experiment was run in which the timing of the addition of the reverse transcriptase was staged after the addition of the T7 mutant RNA polymerase was added. This was done to test whether giving the T7 mutant polymerase a head start in the amplification reaction would yield higher 30 amounts of final product. Therefore, T7 polymerase was added to 5 tubes containing complete reaction mixes. At zero time, reverse transcriptase was added immediately afterwards. Then, all tubes were incubated at 42° C. At, 15 minutes, reverse transcriptase was added to one tube. Other tubes were treated similarly at 30, 45, and 60 minutes. One tube was prepared in which both enzymes were added simultaneously. Incubation was continued for an extra hour at 42° C. Tubes were incubated for 1 hour at 42° C.

To perform the hybridization analysis, 2.5 µl of completed reaction mixes were heated for 2 minutes in a boiling water bath and immediately transferred to 100 µl of denaturation buffer containing 10×SSC and 7.4% formaldehyde. Reactions were incubated at room temperature for 5 minutes to allow the formaldehyde to react with the RNA preventing formation of secondary structure. During the incubation, a piece of nitrocellulose membrane was hydrated and washed in water, then soaked in 10×SCC. The filter is then mounted in a slot blot manifold. Gentle suction is applied to pull through excess liquid. Then each sample was layered into a different slot and gentle suction applied. The filter was removed from the apparatus and dried overnight at room temperature. The filter is then baked at 80° C. for 1 hour to fix the bound nucleic acids. Then, the filter is rehydrated in water for a few minutes and soaked in 10×SCC for a few minutes. Water bath is heated to 50° C., and the filter is then prehybridized in 1×BP (0.5% Bovine Serum Albumin and 0.5% polyvinylpyrrolidone (Mw 40,000)), 5×SSPE (20× =3M NaCl, 200 mM $NaH_2PO_4$, 20 mM EDTA pH 7.4), 1% SDS, 100 ng/ml denatured calf thymus DNA, and 100 ng/ml of an unlabeled irrelevant oligonucleotide, at 50° C. for 30 minutes. The hybridization solution has the same composition except that the AmpSig5-B is added to 120 ng/ml. The filter is hybridized for 1 hour at 50° C., after which it is washed 5 times with 2×SSC for 5 minutes each. A streptavidin-HRP conjugate was diluted in a conjugate diluent solution at 2 µg/ml and added to the washed filter which is then incubated for 30 minutes at room temperature with shaking. The filter is then washed in 2×SSC plus 1% Tween-20 for 3 washes, followed by 2 washes with 2×SSC with no detergent. The filter is lightly blotted and added to a one-step precipitable TMB substrate solution (purchased from Research Diagnostics Inc) until positive staining was observed (about 10 minutes). The blot is then washed in water and dried and photographed.

FIG. 9 shows the results of the slot blot analysis using AmpSig5-B as a probe. Slot 1 shows a very light signal for the template only (with no enzymes). All reactions are compared with these to show how much signal is attributed tot he template. Slot 8 shows the signal obtained when only T7 Mutant RNA polymerase is added (no reverse transcriptase). While the gel analysis showed some transcription, the signal in this slot is identical to the template since the transcript should not hybridize to the probe (as their sequences are collinear). In contrast, the complete reaction (slot 2) which has the enzymes added simultaneously shows the best signal. Lanes 3 through 7 show the time course of addition of reverse transcriptase after addition of T7 mutant RNA polymerase. So 15 minutes means that while T7 mutant polymerase was added a time zero, reverse transcriptase was added 15 minutes later and so on. The zero time sample has a very short lag before the addition of reverse transcriptase since T7 polymerase was added to each tube first, meaning a lag of four tubes before addition of the reverse transcriptase to the zero time tube. The time course result indicates that the best amplification is obtained when both enzymes are added simultaneously. A negative control (linearized pUC 18 DNA) on the blot (not shown) was negative indicating that the hybridization was specific with low background.

Example 5

Effect of Variation in Sequence of Spacer on Amplification

The spacer element used in many of the studies to this point consists of alternating A and G nucleotides. Since these spacer elements are introduced to both strands of the double-stranded intermediate, then transcripts of either strand will contain a AG segment on the 5' end of the transcript and a TC element on the 3' end of the transcript. These segments, since they are perfectly complementary, can hybridize on the same transcript forming a stem-and-loop that may influence amplification. In order to test this hypothesis, the spacer element was modified to minimize possible cross-hybridization with the alternating AG motif. The spacer as shown in Table 2.

TABLE 2

Spacer Variant in Amp011

| Primer | Spacer Structure | Sequence | SEQ ID NO: |
|---|---|---|---|
| Amp011 | Standard | GGGAGAGAGAGAGAGAGA | 27 |
| Amp011Sc | Modified | GGGAGAAGGAGAAAAAGA | 28 |
| | Difference | *   *    *   * | |

An amplification reaction was run exactly as described above except that one set of reactions was run using the modified spacer variant in the Amp011 amplification primer. When the reactions were complete, 2.5 μl of each were analyzed by slot blot hybridization as described above, and the results are shown in FIG. 10. The top panel is the agarose gel electrophoresis pattern of the results, and the lower portion of FIG. 10 is the hybridization analysis. The first lane in FIG. 10 is the template lane showing the mobility of the 350 bp template used for the amplification. The next two lanes have the exact composition of the of the amplification reaction except that only the T7 RNA polymerase was introduced into the reaction. The products seen on the gel reflect only transcription and by products of the reaction. The results show that transcription is not affected by either primer. The next two lanes are complete amplification reactions with both the standard and modified spacer unit. The last lane is the—Template control showing only some reaction by-products at the dye front.

The lower panel shows the same samples (except for the template) as visualized by hybridization analysis. The upper and lower rows are duplicates of the reaction products displayed in the upper panel. Samples 1 and 2 show weak signals attributable in part to the template, and in part to transcription products. Samples 3 and 4 are full amplification reactions showing strong hybridization to the AmpSig5 signal probe. The intensities of both Amp011 and Amp011 Sc are identical. The—template control yields no hybridization signal even though there are apparent side reaction products as exhibited in the gel.

These results show that changes can be made to the spacer that do not affect the efficiency of amplification.

The sequence of the signal probe AmpSig5 is complementary to the lower strand of the template. The first step of the amplification reaction creates upper strands from the transcription reaction is not complementary to the signal probe so will not be detected by AmpSig5. It is not until the reaction performs at least one cycle that transcription products complementary to AmpSig5 are produced. Thus, hybridization analysis using AmpSig5 not only demonstrates that the correct products are being produced, but also proves that the amplification reaction is cycling.

In addition, this analysis shows that both enzymes are necessary to mediate efficient amplification. Without the presence of the RNaseH-Reverse Transcriptase, only very light signals are obtained in the hybridization analysis. The addition of Reverse Transcriptase greatly increases the yield of product. Similar analysis (not shown) that when the reaction only contains reverse transcriptase and no T7 RNA polymerase or mutant, no signals are obtained.

As described above, AmpSig5 should not hybridize to the transcription products from the upper strand and yet the data shows that some signal is indeed obtained. This is in part due to the presence of template some minor background binding of probe and some very weak production of the antisense strand. T7 RNA polymerase, and especially active site mutants have the ability to catalyze primer extension reactions. It is possible in that enough sense strand transcription products were produced in the presence of primers to encourage some very weak production of double strand intermediates and correspondingly very weak production of antisense strands.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of amplifying a target nucleic acid in an aqueous solution with a first and a second primer, said method comprising:
   i.) transcribing an intermediate duplex with a phage-encoded RNA polymerase to form a sense transcription product having a 5' end and a 3' end,
   wherein said intermediate duplex comprises a double-stranded nucleic acid, wherein said double-stranded DNA molecule comprises a first and a second strand,
   wherein said first strand comprises in the following order from 5' to 3':
      a phage-encoded RNA polymerase recognition sequence,
      a first spacer sequence comprising a sequence of from 12 to 20 nucleotides that consists of one nucleotide type or two different nucleotide types, and
      a first target complementary sequence which can bind to a segment of said target nucleic acid,
   wherein said second strand comprises in the following order from 5' to 3':
      a second target complementary sequence which can bind to a segment of said target nucleic acid,
      a second spacer sequence comprising a sequence of from 12 to 20 nucleotides that consists of one nucleotide type or two different nucleotide types, and
      a phage-encoded RNA polymerase recognition sequence,
   wherein said transcribing takes place in the presence of Mn++, with all four dNTPs, and with those rNTPs represented in said first spacer sequence;
   ii.) hybridizing said second primer to said sense transcription product to form a second primer-sense transcription product complex,
   wherein said second primer comprises in the following order from 5' to 3':
      a phage-encoded RNA polymerase recognition sequence,
      said second spacer sequence, and
      said second target complementary sequence which can bind to a 3' segment of said target nucleic acid;
   iii.) extending said second primer-sense transcription product complex with a Reverse Transcriptase that lacks RNAseH activity to form a first amplification duplex;
   iv.) transcribing said first amplification duplex with a phage-encoded RNA polymerase, in the presence of Mn++, with all four dNTPs, and with those rNTPs represented in said second spacer sequence, to form an antisense transcription product;
   v.) hybridizing said first primer to said antisense transcription product to form a first primer-antisense transcription product complex,
   wherein said first primer comprises in the following order from 5' to 3':
      a phage-encoded RNA polymerase recognition sequence,
      said first spacer sequence, and
      said first target complementary sequence which can bind to a 5' segment of said target nucleic acid;
   vi.) extending said first primer-antisense transcription product complex with a Reverse Transcriptase that lacks RNAseH activity to form a second amplification duplex; and
   vii.) transcribing said second amplification duplex with a phage-encoded RNA polymerase, in the presence of Mn++, with all four dNTPs, and with those rNTPs represented in said first spacer sequence to form said sense transcription product.

2. The method of claim 1, wherein the method further comprises repetitively carrying out steps i to vii.

3. The method of claim 1, wherein said first or said second spacer sequence comprises a nucleotide sequence having the formula (XY)n,
   wherein n is from 6 to 10, wherein X and Y are independently selected from the group consisting of an adenine nucleotide, a guanine nucleotide, a cytosine nucleotide, and a thymidine nucleotide, wherein X and Y are not the same.

4. The method of claim 3, wherein X is an adenine nucleotide and Y is a guanine nucleotide.

5. The method of claim 4, wherein n is 9.

6. The method of claim 4, wherein the rNTPs are rATP and rGTP.

7. The method of claim 1, wherein said first or said second spacer sequence comprises a nucleotide sequence having the formula $(X)n$, wherein n is from 12 to 20, wherein X is selected from the group consisting of an adenine nucleotide, a guanine nucleotide, a cytosine nucleotide, and a thymidine nucleotide.

8. The method of claim 7, wherein n is 18.

9. The method of claim 1, wherein said sense and antisense transcription products comprise a nucleic acid strand comprising both ribonucleotides and deoxyribonucleotides.

10. The method of claim 1, wherein said first and said second amplification duplexes consist of deoxyribonucleotides and ribonucleotides.

11. The method of claim 1, wherein said method is carried out at a single temperature.

12. The method of claim 1, wherein said method is carried out at a single temperature of between 25° C. and 55° C.

13. The method of claim 1, wherein the method is carried out at a single temperature of greater than 50° C.

14. The method of claim 1, wherein said intermediate duplex comprises a double-stranded DNA comprising one complete primer sequence followed by the entire sequence that is to be amplified.

15. The method of claim 1, wherein said intermediate duplex is formed from double-stranded DNA, single-stranded DNA, or RNA.

16. The method of claim 1, wherein said intermediate duplex is formed by the process comprising the following steps of:

denaturing a double-stranded DNA target to form an upper strand and a lower strand;

hybridizing said first primer to said lower strand to form a first primer-lower strand complex;

extending said first primer-lower strand complex with a Reverse Transcriptase that lacks RNAseH activity or with a DNA Polymerase to form a first long sense strand product-lower strand complex;

denaturing said first long sense strand product-lower strand complex into a first long sense strand product and said lower strand;

hybridizing said second primer to said first long sense strand product to form a second primer-first long sense strand product; and extending said first primer-first long antisense strand product with a Reverse Transcriptase that lacks RNAseH activity or with a DNA Polymerase to yield said intermediate duplex.

17. The method of claim 1, wherein said intermediate duplex is formed by the process comprising the following steps of:

denaturing a double-stranded DNA target to form an upper strand and a lower strand;

hybridizing said first primer to said lower strand to form a first primer-lower strand complex;

extending said first primer-lower strand complex with a Reverse Transcriptase that lacks RNAseH activity or with a DNA Polymerase to form a first long sense strand product-lower strand complex, wherein said first long sense strand product has a 5' and a 3' end;

displacing said first sense strand product from said lower strand by:

hybridizing a bumper oligonucleotide to a subsequence on said lower strand adjacent to said 5' end of said first sense strand product on the first sense strand product-lower strand complex;

extending said bumper oligonucleotide with a Reverse Transcriptase that lacks RNAseH activity or with a DNA Polymerase, thereby displacing said first sense strand product;

hybridizing said second primer to said first long sense strand product to form a second primer-first long sense strand product; and extending said first primer-first long antisense strand product with a Reverse Transcriptase that lacks RNAseH activity or with a DNA Polymerase to yield said intermediate duplex.

18. The method of claim 1, wherein said intermediate duplex is formed by the process comprising the following steps of:

hybridizing said second primer to a target RNA molecule to form a second primer-RNA template complex;

extending said second primer-target RNA molecule complex with a Reverse Transcriptase that lacks RNAseH activity or a DNA Polymerase to form a first long antisense strand product-template complex, wherein said first long antisense strand product has a 5' and a 3' end;

displacing said first long antisense strand product from said target RNA molecule by:

hybridizing a bumper oligonucleotide to a subsequence on said target RINA molecule adjacent to said 5' end of said first sense strand product on the first sense strand product-lower strand complex;

extending said bumper oligonucleotide with a Reverse Transcriptase that lacks RNAseH activity or with a DNA Polymerase, thereby displacing said first long antisense strand product;

hybridizing said first primer to said first long antisense strand product to form a first primer-first long antisense strand product complex; and extending said first primer-first long antisense strand product with a Reverse Transcriptase that lacks RNAseH activity or with a DNA Polymerase to yield said intermediate duplex.

19. The method of claim 1, wherein said intermediate duplex is formed by the process comprising the following steps of:

hybridizing said second primer to a single-stranded target RNA molecule to form a second primer-RNA template complex;

extending said second primer-RNA template complex with a Reverse Transcriptase that lacks RNAseH activity or a DNA Polymerase to form a first long antisense strand product-template complex;

denaturing said first long antisense strand product-RNA template complex into a first long antisense strand product and said single-stranded RNA molecule;

hybridizing said first primer to said first long antisense strand product to form a first primer-first long antisense strand product complex; and extending said first primer-first long antisense strand product with a Reverse Transcriptase that lacks RNAseH activity or with a DNA Polymerase to yield said intermediate duplex.

20. The method of claim 1, wherein said phage-encoded RNA polymerase is polymerase selected from the group consisting of: a T7 RNA polymerase, a T4 RNA polymerase, a T3 RNA polymerase, a SP6 RNA polymerase and a K11 RNA polymerase.

21. The method of claim 20, wherein said phage-encoded RNA polymerase is a mutant phage-encoded RNA polymerase that is competent to incorporate dNTPs into a template nucleic acid.

22. The method of claim 21, wherein said phage-encoded RNA polymerase is a T7 RNA polymerase.

23. The method of claim 22, wherein said T7 RNA polymerase contains a Y639F mutation.

24. The method of claim 22, wherein said T7 RNA polymerase contains a S641A mutation.

25. The method of claim 22, wherein said T7 RNA polymerase contains at least two mutations.

26. The method of claim 1, wherein said Mn++ is present in a concentration of between 10 µM to 20 mM.

27. The method of claim 26, wherein said concentration is 10 mM.

28. The method of claim 1, wherein said target nucleic acid is single-stranded DNA.

29. The method of claim 1, wherein the target nucleic acid is comprised of RNA.

30. The method of claim 1, further detecting said sense transcription product, said antisense transcription product, said first amplification duplex, or said second amplification duplex, wherein said detecting comprises hybridizing a detection oligonucleotide comprising a detectable moiety, wherein said detection oligonucleotide is complementary to a subsequence of said sense transcription product, said antisense transcription product, said first amplification duplex, or said second amplification duplex.

* * * * *